(12) United States Patent
Kutchan et al.

(10) Patent No.: US 7,514,251 B2
(45) Date of Patent: Apr. 7, 2009

(54) **O-METHYLTRANSFERASES OF TETRAHYDROBENZYLISOQUINOLINE ALKALOID BIOSYNTHESIS IN *PAPAVER SOMNIFERUM***

(75) Inventors: Toni M. Kutchan, St. Louis, MO (US); Anan Ounaroon, Bangkae (TH); Stefanie Haase, Werben (DE); Susanne Frick, Augsburg (DE)

(73) Assignee: Donald Danforth Plant Science Center, St. Louis, MO (US)

( * ) Notice: Subject to any disclaimer, the term of this patent is extended or adjusted under 35 U.S.C. 154(b) by 254 days.

(21) Appl. No.: 10/888,656

(22) Filed: Jul. 8, 2004

(65) Prior Publication Data

US 2005/0106588 A1 May 19, 2005

(30) Foreign Application Priority Data

Sep. 3, 2003 (EP) .................. 03020023

(51) Int. Cl.
*C12N 9/10* (2006.01)
*C12N 5/10* (2006.01)
*C07H 21/04* (2006.01)

(52) U.S. Cl. ............... 435/193; 435/419; 536/23.2

(58) Field of Classification Search ............... None
See application file for complete search history.

(56) References Cited

OTHER PUBLICATIONS

Li et al., "A novel multifunctional O-methyltransferase implicated in a dual methylation pathway associated with lignin biosynthesis in loblolly pine." Proc. Natl. Acad. Sci. U.S.A. 94:5461-5466 (1997).*
Facchini and Park; Genbank Accession AY217335; National Center for Biotechnology Information GenBank database; Aug. 2, 2003.
Facchini et al.; "Developmental and inducible accumulation of gene transcripts involved in alkaloid biosynthesis in opium poppy"; Phytochemistry; (2003); pp. 177-186; vol. 64; 2003 Elsevier Ltd.
Frick et al.; "Combinatorial biochemistry in plants: the case of O-methyltransferases"; Phytochemistry; (2001); pp. 1-4; vol. 56; 2001 Elsevier Science Ltd.
Frick et al.; "Molecular cloning and functional expression of O-methlytransferases common to isoquinoline alkaloid and phenylpropanoid biosynthesis."; The Plant Journal; (1999); pp. 329-339; vol. 17, No. 4; 1999 Blackwell Science Ltd.
Joshi et al.; "Conserved sequence motifs in plant S-adenosyl-L-methionine-dependent methyltransferases", Plant Molecular Biology; (1998); pp. 663-674; vol. 37; 1998 Kluwer Academic Publishers.
Ounaroon et al.; "(R,S)-Reticuline 7-O-methyltransferase and (R,S)-norcoclaurine 6-O-methyltransferase of *Papaver somniferum*—cDNA cloning and characterization of methyl transfer enzymes of alkaloid biosynthesis in opium poppy"; The Plant Journal; (2003); pp. 808-819; vol. 36; 2003 Blackwell Publishing Ltd.
Zubieta et al.; "Structures of two natural product methyltransferases reveal the basis for substrate specificity in plant O-methyltransferases"; Nat. Struct. Biol.; (2001); pp. 271-279; vol. 8, No. 3; 2001 Nature Publishing Group.
Ounaroon, Anan; "Molecular Cloning and Functional Expression of Three-O-methyltransferases from *Papaver somniferum L*."; Doctoral Thesis; Sep. 11, 2002; Revelant pp. 31-43, -50-78, and 85-96.

* cited by examiner

*Primary Examiner*—Andrew D. Kosar
*Assistant Examiner*—Kagnew Gebreyesus
(74) *Attorney, Agent, or Firm*—Thompson Coburn LLP; Charles P. Romano

(57) ABSTRACT

The present invention relates to methyl transfer enzymes involved in alkaloid biosynthesis in opium poppy. More particularly, the invention relates to proteins having (R,S)-reticuline 7-O-methyltransferase activity, to proteins having (R,S)-norcoclaurine 6-O-methyltransferase activity and to derivatives and analogues of these proteins. The invention also relates to nucleic acid molecules encoding the proteins, and their derivatives and analogues, and to their use in the production of methylated catechols and tetrahydrobenzylisoquinolines.

3 Claims, 16 Drawing Sheets

Figure 1:
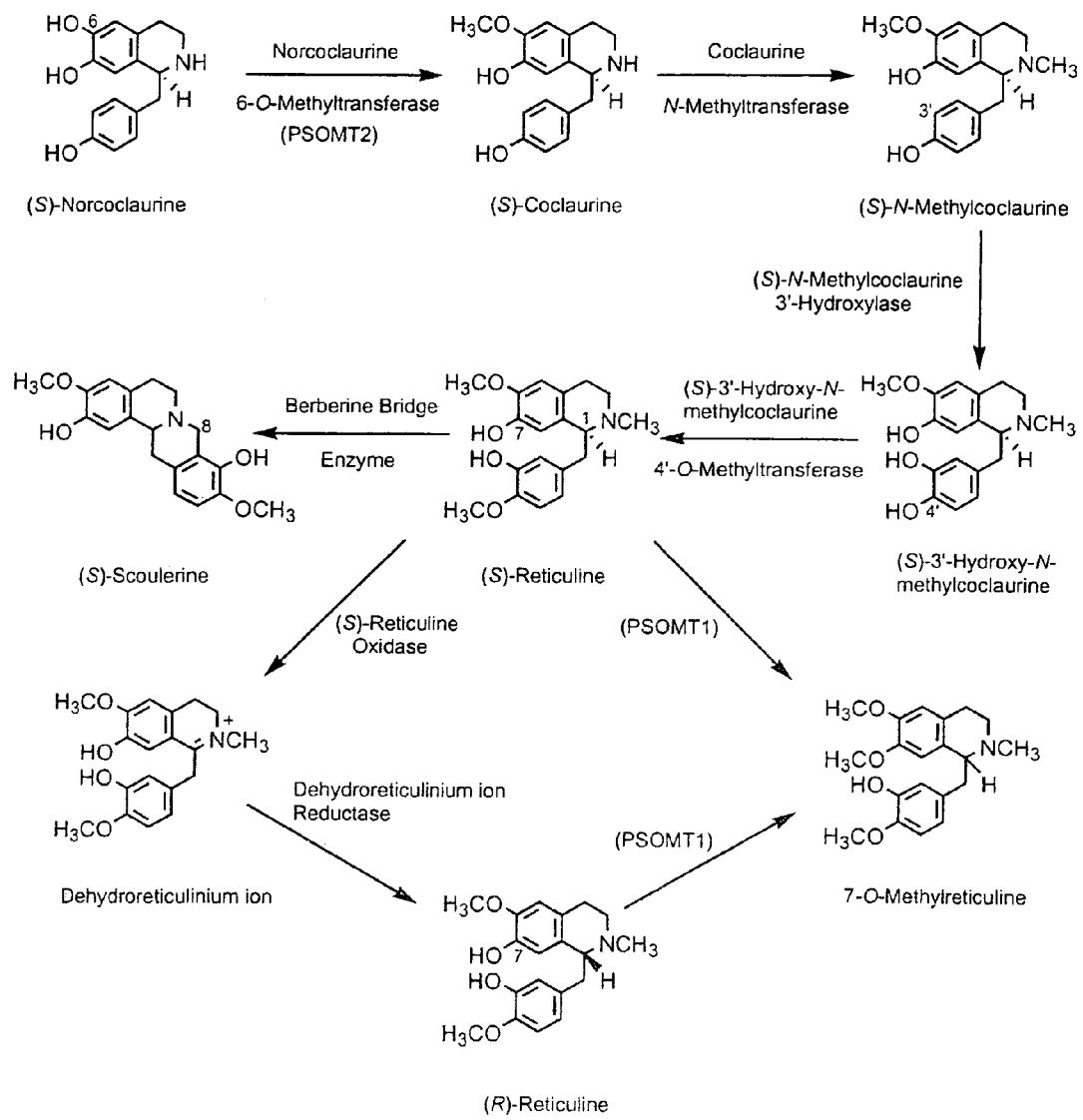

| | |
|---|---|
| PSOMT1 | MDTAEERLKGQAEIWEHMFAFVDSMA-LKCAVELGIPDIINSHGRPVTIS |
| PSOMT2 | METVSKIDQQNQAKIWKQIYGFAESLVLKCAVQLEIAETLHNNVKPMSLS |
| | |
| PSOMT1 | EIVDSLKTNTPSSSPNIDYLTRIMRLLVHKRLFTSELHQESNQLLYNLTR |
| PSOMT2 | ELASKLPVAQPVNEDRLFRI---MRYLVHMELFKIDATTQKYSLAPPAKY |
| | |
| PSOMT1 | SSKWLLKDSKFNLSPLVLWETNPILLKPWQYLGKCAQEKSSPFERAHGCE |
| PSOMT2 | LLRGWEKSMVDSILCINDKDFLAPWHHLGDGLTGNCDAFEKALGKSIWVY |
| | motif A |
| PSOMT1 | IWDLALADPKFNNFLNGAMQCSTTTIINEMLLEYKDGFSGIAGSLVDVGG |
| PSOMT2 | MSVNPEKNQLFNAAMACDTRLVTSALANECKSIFSDGIST----LVDVGG |
| | motif J          motif K |
| PSOMT1 | GTGSIIAEIVKAHPHIQGINFDLPHVVATAAEFPGVKHVGGDMFVDIPEA |
| PSOMT2 | GTGTAVKAISKAFPDIKCTIYDLPHVIADSPEIPNITKISGDMFKSIPSA |
| | motif B                              motif C |
| PSOMT1 | DAVIMKWILHDWSDEDCTIILKNCYRAIRKKKNGKVIIVDCVLRPDGNDL |
| PSOMT2 | DAIFMKCILHDWNDDECIQILKRCKEAL--PKGGKVIIVDVVIDMDSTHP |
| | motif L |
| PSOMT1 | FDKMGLIFDVLMMAHTTAGKERTEAEWKILLNNAGFPRYNVIRTPAFPCI |
| PSOMT2 | YAKIRLTLDLDMMLNT-GGKERTKEEWKTLFDAAGFASHKVTQISAVQSV |
| | |
| PSOMT1 | IEAFPE |
| PSOMT2 | IEAYPY |

Figure 3

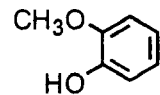
Guaiacol
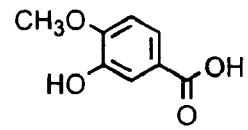
Isovanillic acid
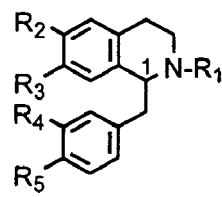
| Substrate | $R_1$ | $R_2$ | $R_3$ | $R_4$ | $R_5$ |
|---|---|---|---|---|---|
| (R,S)-Norcoclaurine | H | OH | OH | H | OH |
| (R)-Norprotosinomenine | H | OH | $OCH_3$ | OH | $OCH_3$ |
| (S)-Norprotosinomenine | H | OH | $OCH_3$ | OH | $OCH_3$ |
| (R)-Reticuline | $CH_3$ | $OCH_3$ | OH | OH | $OCH_3$ |
| (S)-Reticuline | $CH_3$ | $OCH_3$ | OH | OH | $OCH_3$ |
| (R,S)-Orientaline | $CH_3$ | $OCH_3$ | OH | $OCH_3$ | OH |
| (R)-Protosinomenine | $CH_3$ | OH | $OCH_3$ | OH | $OCH_3$ |
| (R,S)-Isoorientaline | $CH_3$ | OH | $OCH_3$ | $OCH_3$ | OH |
Figure 6

```
gaaaacaaaa cataaacaca atttattcag agatatctgg atggatactg cagaagaaag      60
gttgaaaggg caagctgaaa tatgggagca tatgttcgca ttcgtggatt caatggcatt     120
gaaatgtgca gttgagcttg cataccaga cataataaac tctcatggtc gtccggtcac     180
aatatctgag atcgtcgaca gtttgaaaac aaacacacca tcatcatctc ccaacatcga     240
ttatcttaca cgtataatga gactactggt tcacaagagg ctatttactt ctgaacttca     300
tcaagaaagt aaccaacttc tctataattt aactcgatca tcaaaatggc tactaaaaga     360
ttccaagttt aatctgtcac cactggtttt atgggaaact aatccgatat tactaaaacc     420
atggcaatat ttgggcaagt gtgctcaaga aaaagttct ccatttgaga gagctcatgg     480
atgtgagatt tgggatcttg ctttagctga tcctaagttt aataatttcc ttaacggtgc     540
aatgcaatgt tcgactacaa caataatcaa cgagatgctg cttgaatata agatggatt      600
tagtggtata gcaggatcgc ttgttgatgt cggggtggg accgggtcga taatcgctga     660
aatagttaag gctcatccac acatacaagg catcaatttt gatctaccac atgtagtggc     720
tacagcggct gaatttccag gggtgaagca tgtcggtggt gatatgtttg tcgatattcc     780
ggaagctgat gctgtcatca tgaagtggat attcacgac tggagtgacg aagactgtac     840
aattatactg aagaattgtt accgagcaat aagaaagaag aaaaacggaa aagtcataat     900
tgttgattgt gtgttgcgac cagatggaaa tgacttattc gataaaatgg gattgatatt     960
tgatgtgctg atgatggcac atactacagc tggaaaagaa agaacagaag cggaatggaa    1020
gatcttatta aataatgcag gttttcctcg ttacaatgtc attcgaactc cggcatttcc    1080
ttgcatcatc gaggcctttc cagaataatg atcaaggtgc agctatggta gcccaacgat    1140
actctcaagc tatatatatg atatttccaa aagaatgtgt tctctttgtt gtgcatgttt    1200
tgtagagtgt ggtaactttg gaaagaccat ttacaaatag ctatgctatt tgttggctag    1260
ctaagggtca ggttcctaca aataattca gaactttatg ttttgagtg gtaataaaac     1320
aattctcctg tgagagagct gttaccttgt ctgttatctg tattgctatc cttagacatc    1380
tgggggggtg gaatgtattc tgattttgcg ttttacgta aaaaaaaaa aaaaaaa        1437
```

Figure 8

```
MDTAEERLKG QAEIWEHMFA FVDSMALKCA VELGIPDIIN SHGRPVTISE IVDSLKTNTP        60
SSSPNIDYLT RIMRLLVHKR LFTSELHQES NQLLYNLTRS SKWLLKDSKF NLSPLVLWET       120
NPILLKPWQY LGKCAQEKSS PFERAHGCEI WDLALADPKF NNFLNGAMQC STTTIINEML       180
LEYKDGFSGI AGSLVDVGGG TGSIIAEIVK AHPHIQGINF DLPHVVATAA EFPGVKHVGG       240
DMFVDIPEAD AVIMKWILHD WSDEDCTIIL KNCYRAIRKK KNGKVIIVDC VLRPDGNDLF       300
DKMGLIFDVL MMAHTTAGKE RTEAEWKILL NNAGFPRYNV IRTPAFPCII EAFPE            355
```

Figure 9

```
gagctcaaatcattcaatcattcttctcatcaacagagagaaatgaaacagtaagcaagattg
atcaacaaaaccaagcaaaaatctggaaacaaattacggtttcgcagaatcactagttctgaaatgtgcagtccaactag
agattgctgaaacacttcacaacaatgtcaaaccatgtcttatcgaattggcatcgaaacttcccgttgctcaaccg
ttaacgaagaccgtctgttccgattatgcgttcggttcacatggagctcttcaaaatagatgctaccacgcagaaat
actcattagctccaccagctaagtatttgttgagaggctgggagaaatcaatggttgattcaatttatgcataaatgata
aggatttcttagctccatggcaccatttaggcgacgttgaccggttgaccgtttgacgctttgagaaagcgttggggaaga
gtatttgggtgtatatgagtgagtgcaaagtattttcagcaatggcttgtgatactagattggtta
cttctgcattggctaatgagtgagtgcaaagtatttcagatattaagtgcactatctatgatcttcctcatgttgatgtcgcggtggtacgggta
ctgcagtgaaagccatatctcaaagctttcccggatattaagtgcactatctatgatcttcctcatgttcctctagtcgattctc
cngaaatcccaatatcactaaaattctggagatatgttcaagtctcaagtcaagtgccatcttcatgaagtgca
tacttcacgactggaacgatgacgatagacatggattcgactcatccatcgactgaaagaagcattaccacactggattggatatgatgc
ttatcgtggatgtcgtgaaagagagacaaagaatggaagacacttttgatgccgctgttttgctagccacaagtca
ttaacactggtggaaagagagaaccaaaagaatggaagacacttttgatgccgctgttttgctagccacaaagtca
ctcagatatctgctgtcaatctgtaattgaggcttataacaattgcaagatgactcaactcgcattggattaatgtttt
gttgcttctcttttgattatgtttatgtttataacaattgcaagatgactccaactcgcattggattaatgtttt
tcgtttacttacttttctagatattttgaggggctttgtttaaatttgatatcccacgtttgtaactgtaaagagtagagt
ggatgaatgatactccctccgtttccaaaaaaaaaaaaaaaaaaaa
```

Figure 10

```
atggaaacagtaagcaagattgatcaacaaaaccaagcaaaaatctggaaacaaatttacggtttcgcagaatcactagt
tctgaaatgtgcagtccaactagagattgctgaaacacttcacaacaatgtcaaacccatgtctttatccgaattggcat
cgaaacttcccgttgctcaacccgttaacgaagaccgtctgttccgaattatgcgttacttggttcacatggagctcttc
aaaatagatgctaccacgcagaaatactcattagttccaccagctaagtatttgttgagaggctgggagaaatcaatggt
tgattcaatttta tgcataaatgataaggatttcttagctccatggcaccatttaggcgacggtttgaccggtaactgtg
acgcttttgagaaagcgttggggaagagtatttgggtgtatatgagtgaaaatcctgaaaagaatcaattgtttaatgca
gcaatggcttgtgatactagattggttacttctgcattggctaatgagtgcaaaagtattttcagtgatggaatcagtac
actggttgatgtcggcggtggtacgggtactgcagtgaaagccatatctaaagcttttccggatattaagtgcactatct
atgatcttcctcatgtcatagctgattctcctgaaatccccaatatcactaaaattcctggagatatgttcaagtctatt
cctagtgctgatggcatcttcatgaagtgcatacttcacgactggaacgatgacgaatgcattcaaatcttgaagagatg
caaagaagcattaccaaaagttggcaaagttattatcgtggatgtcgtgatagacatggattcgactcatccatatgcaa
aaattagactcacactggatttggatatgatgcttaacactggtggaaaagagagaaccaaagaagaatggaagacactt
tttgatgccgctggttttgctagccacaaagtcactcagatatctgctgtccaatctgtaattgaggcttacccttatta
a
```

Figure 11

```
   1 gcagctaaag tgtctaaaca gagagaaatg gaaacagtaa gcaagattga tcaacaaaac
  61 caagcaaaaa tctggaaaca aatttacggt ttcgcagaat cactagttct gaaatgtgca
 121 gtccaactag agattgctga aacacttcac aacaatgtca aacccatgtc tttatccgaa
 181 ttggcatcga aacttcccgt tgctcaaccc gttaacgaag accgtctgtt ccgaattatg
 241 cgttacttgg ttcacatgga gctcttcaaa atagatgcta ccacgcagaa atactcatta
 301 gctccaccag ctaagtattt gttgagaggc tgggagaaat caatggttga ttcaattttta
 361 tgcataaatg ataaggattt cttagctcca tggcaccatt taggcgacgg tttgaccggt
 421 aactgtgacg cttttgagaa agcgttgggg aagagtattt gggtgtatat gagtgaaaat
 481 cctgaaaaga atcaattgtt taatgcagca atggcttgtg atactagatt ggttacttct
 541 gcattggcta atgagtgcaa aagtattttc agtgatggaa tcagtacact ggttgatgtc
 601 ggcggtggta cgggtactgc agtgaaagcc atatctaaag cttttccgga tattaagtgc
 661 actatctatg atcttcctca tgtcatagct gattctcctg aaatccccaa tatcactaaa
 721 atttctggag atatgttcaa gtctattcct agtgctgatg ccatcttcat gaagtgcata
 781 cttcacgact ggaacgatga tgaatgcatt caaatcttga agagatgcaa agaagcatta
 841 ccaaaagttg gcaaagttat tatcgtggat gtcgtgatag acatggattc gactcatcca
 901 tatgcaaaaa ttagactcac actggatttg gatatgatgc ttaacactgg tggaaaagag
 961 agaaccaaag aagaatggaa gacacttttt gatgccgctg gttttgctag ccacaaagtc
1021 actcagatat ctgctgtcca atctgtaatt gaggcttacc cttattaagg aacattttaa
1081 ccggttttcc ctttgattaa ttgttgcttt ctctttggat tatgtttatg tttataacaa
1141 ttgcaagatg aatgaatttc caacttgcat tggattaaaa aaaaaaaaaa aaaa
```

Figure 12

METVSKIDQQNQAKIWKQIYGFAESLVLKCAVQLEIAETLHNNVKPMSLSELASKLPVAQPVNEDRLFRIMRYLVHMELF
KIDATTQKYSLAVPAKYLLRGWEKSMVDSILCINDKDFLAPWHHLGDGLTGNCDAFEKALGKSIWVYMSENPEKNQLFNA
AMACDTRLVTSALANECKSIFSDGISTLVDVGGGTGTAVKAISKAFPDIKCTIYDLPHVIADSPEIPNITKIPGDMFKSI
PSADGIFMKCILHDWNDDECIQILKRCKEALPKVGKVIIVDVVIDMDSTHPYAKIRLTLDLDMMLNTGGKERTKEEWKTL
FDAAGFASHKVTQISAVQSVIEAYPY

Figure 13

```
METVSKIDQQNQAKIWKQIYGFAESLVLKCAVQLEIAETLHNNVKPMSLSELASKLPVAQPVNEDR
LFRIMRYLVHMELFKIDATTQKYSLAPPAKYLLRGWEKSMVDSILCINDKDFLAPWHHLGDGLTGN
CDAFEKALGKSIWVYMSENPEKNQLFNAAMACDTRLVTSALANECKSIFSDGISTLVDVGGGTGTA
VKAISKAFPDIKCTIYDLPHVIADSPEIPNITKISGDMFKSIPSADAIFMKCILHDWNDDECIQIL
KRCKEALPKVGKVIIVDVVIDMDSTHPYAKIRLTLDLDMMLNTGGKERTKEEWKTLFDAAGFASHK
VTQISAVQSVIEAYPY
```

Figure 14

```
METVSKIDQQNQAKIWKQIYGFAESLVLKCAVQLEIAETLHNNVKPMSLSELASKLPVAQPVNEDRLFR  AO
METVSKIDQQNQAKIWKQIYGFAESLVLKCAVQLEIAETLHNNVKPMSLSELASKLPVAQPVNEDRLFR  SH
METVSKIDQQNQAKIWKQIYGFAESLVLKCAVQLEIAETLHNNVKPMSLSELASKLPVAQPVNEDRLFR  PF

IMRYLVHMELFKIDATTQKYSLAPPAKYLLRGWEKSMVDSILCINDKDFLAPWHHLGDGLTGNCDAFEK  AO
IMRYLVHMELFKIDATTQKYSLAVPAKYLLRGWEKSMVDSILCINDKDFLAPWHHLGDGLTGNCDAFEK  SH
IMRYLVHMELFKIDATTQKYSLAPPAKYLLRGWEKSMVDSILCINDKDFLAPWHHLGDGLTGNCDAFEK  PF

ALGKSIWVYMSVNPEKNQLFNAAMACDTRLVTSALANECKSIFSDGISTLVDVGGGTGTAVKAISKAFP  AO
ALGKSIWVYMSENPEKNQLFNAAMACDTRLVTSALANECKSIFSDGISTLVDVGGGTGTAVKAISKAFP  SH
ALGKSIWVYMSENPEKNQLFNAAMACDTRLVTSALANECKSIFSDGISTLVDVGGGTGTAVKAISKAFP  PF

DIKCTIYDLPHVIADSPEIPNITKISGDMFKSIPSADAIFMKCILHDWNDDECIQILKRCKEALPKGGK  AO
DIKCTIYDLPHVIADSPEIPNITKIPGDMFKSIPSADGIFMKCILHDWNDDECIQILKRCKEALPKVGK  SH
DIKCTIYDLPHVIADSPEIPNITKISGDMFKSIPSADAIFMKCILHDWNDDECIQILKRCKEALPKVGK  PF

VIIVDVVIDMDSTHPYAKIRLTLDLDMMLNTGGKERTKEEWKTLFDAAGFASHKVTQISAVQSVIEAYP  AO
VIIVDVVIDMDSTHPYAKIRLTLDLDMMLNTGGKERTKEEWKTLFDAAGFASHKVTQISAVQSVIEAYP  SH
VIIVDVVIDMDSTHPYAKIRLTLDLDMMLNTGGKERTKEEWKTLFDAAGFASHKVTQISAVQSVIEAYP  PF

Y
Y
Y
```

Figure 15

METVSKIDQQNQAKIWKQIYGFAESLVLKCAVQLEIAETLHNNVKPMSLSELASKLPVAQPVNEDRLFR 69

IMRYLVHMELFKIDATTQKYSLA[X]PAKYLLRGWEKSMVDSILCINDKDFLAPWHHLGDGLTGNCDAFEK 138

ALGKSIWVYMS[X]NPEKNQLFNAAMACDTRLVTSALANECKSIFSDGISTLVDVGGGTGTAVKAISKAFP 207

DIKCTIYDLPHVIADSPEIPNITKI[X]GDMFKSIPSAD[X]IFMKCILHDWNDDECIQILKRCKEALPK[X]GK 276

VIIVDVVIDMDSTHPYAKIRLTLDLDMMLNTGGKERTKEEWKTLFDAAGFASHKVTQISAVQSVIEAYP 345

Y 346

FIGURE 16

SEQUENCE LISTING

<160> NUMBER OF SEQ ID NOS: 24

<210> SEQ ID NO 1
<211> LENGTH: 1437
<212> TYPE: DNA
<213> ORGANISM: Papaver somniferum

```
<220> FEATURE:
<221> NAME/KEY: CDS
<222> LOCATION: (41)..(1108)
<223> OTHER INFORMATION:

<400> SEQUENCE: 1 gaaacaaaa cataaacaca atttattcag agatatctgg atg gat act gca gaa      55
                                            Met Asp Thr Ala Glu
                                            1               5 gaa agg ttg aaa ggg caa gct gaa ata tgg gag cat atg ttc gca ttc    103
Glu Arg Leu Lys Gly Gln Ala Glu Ile Trp Glu His Met Phe Ala Phe
            10                  15                  20 gtg gat tca atg gca ttg aaa tgt gca gtt gag ctt ggc ata cca gac    151
Val Asp Ser Met Ala Leu Lys Cys Ala Val Glu Leu Gly Ile Pro Asp
        25                  30                  35 ata ata aac tct cat ggt cgt ccg gtc aca ata tct gag atc gtc gac    199
Ile Ile Asn Ser His Gly Arg Pro Val Thr Ile Ser Glu Ile Val Asp
    40                  45                  50 agt ttg aaa aca aac aca cca tca tca tct ccc aac atc gat tat ctt    247
Ser Leu Lys Thr Asn Thr Pro Ser Ser Ser Pro Asn Ile Asp Tyr Leu
55                  60                  65 aca cgt ata atg aga cta ctg gtt cac aag agg cta ttt act tct gaa    295
Thr Arg Ile Met Arg Leu Leu Val His Lys Arg Leu Phe Thr Ser Glu
70                  75                  80                  85 ctt cat caa gaa agt aac caa ctt ctc tat aat tta act cga tca tca    343
Leu His Gln Glu Ser Asn Gln Leu Leu Tyr Asn Leu Thr Arg Ser Ser
                90                  95                 100 aaa tgg cta cta aaa gat tcc aag ttt aat ctg tca cca ctg gtt tta    391
Lys Trp Leu Leu Lys Asp Ser Lys Phe Asn Leu Ser Pro Leu Val Leu
            105                 110                 115 tgg gaa act aat ccg ata tta cta aaa cca tgg caa tat ttg ggc aag    439
Trp Glu Thr Asn Pro Ile Leu Leu Lys Pro Trp Gln Tyr Leu Gly Lys
        120                 125                 130 tgt gct caa gaa aaa agt tct cca ttt gag aga gct cat gga tgt gag    487
Cys Ala Gln Glu Lys Ser Ser Pro Phe Glu Arg Ala His Gly Cys Glu
    135                 140                 145 att tgg gat ctt gct tta gct gat cct aag ttt aat aat ttc ctt aac    535
Ile Trp Asp Leu Ala Leu Ala Asp Pro Lys Phe Asn Asn Phe Leu Asn
150                 155                 160                 165 ggt gca atg caa tgt tcg act aca aca ata atc aac gag atg ctg ctt    583
Gly Ala Met Gln Cys Ser Thr Thr Thr Ile Ile Asn Glu Met Leu Leu
                170                 175                 180 gaa tat aaa gat gga ttt agt ggt ata gca gga tcg ctt gtt gat gtc    631
Glu Tyr Lys Asp Gly Phe Ser Gly Ile Ala Gly Ser Leu Val Asp Val
            185                 190                 195 ggg ggt ggg acc ggg tcg ata atc gct gaa ata gtt aag gct cat cca    679
Gly Gly Gly Thr Gly Ser Ile Ile Ala Glu Ile Val Lys Ala His Pro
        200                 205                 210 cac ata caa ggc atc aat ttt gat cta cca cat gta gtg gct aca gcg    727
His Ile Gln Gly Ile Asn Phe Asp Leu Pro His Val Val Ala Thr Ala
    215                 220                 225 gct gaa ttt cca ggg gtg aag cat gtc ggt ggt gat atg ttt gtc gat    775
Ala Glu Phe Pro Gly Val Lys His Val Gly Gly Asp Met Phe Val Asp
230                 235                 240                 245 att ccg gaa gct gat gct gtc atc atg aag tgg ata ttg cac gac tgg    823
Ile Pro Glu Ala Asp Ala Val Ile Met Lys Trp Ile Leu His Asp Trp
                250                 255                 260 agt gac gaa gac tgt aca att ata ctg aag aat tgt tac cga gca ata    871
Ser Asp Glu Asp Cys Thr Ile Ile Leu Lys Asn Cys Tyr Arg Ala Ile
            265                 270                 275
```

-continued

| | | |
|---|---|---|
| aga aag aag aaa aac gga aaa gtc ata att gtt gat tgt gtg ttg cga<br>Arg Lys Lys Lys Asn Gly Lys Val Ile Ile Val Asp Cys Val Leu Arg<br>    280        285        290 | | 919 |
| cca gat gga aat gac tta ttc gat aaa atg gga ttg ata ttt gat gtg<br>Pro Asp Gly Asn Asp Leu Phe Asp Lys Met Gly Leu Ile Phe Asp Val<br>295        300        305 | | 967 |
| ctg atg atg gca cat act aca gct gga aaa gaa aga aca gaa gcg gaa<br>Leu Met Met Ala His Thr Thr Ala Gly Lys Glu Arg Thr Glu Ala Glu<br>310        315       320       325 | | 1015 |
| tgg aag atc tta tta aat aat gca ggt ttt cct cgt tac aat gtc att<br>Trp Lys Ile Leu Leu Asn Asn Ala Gly Phe Pro Arg Tyr Asn Val Ile<br>        330       335       340 | | 1063 |
| cga act ccg gca ttt cct tgc atc atc gag gcc ttt cca gaa taa<br>Arg Thr Pro Ala Phe Pro Cys Ile Ile Glu Ala Phe Pro Glu<br>     345       350      355 | | 1108 |
| tgatcaaggt gcagctatgg tagcccaacg atactctcaa gctatatata tgatatttcc | | 1168 |
| aaaagaatgt gttctctttg ttgtgcatgt tttgtagagt gtggtaactt tggaaagacc | | 1228 |
| atttacaaat agctatgcta tttgttggct agctaagggt caggttccta caaaataatt | | 1288 |
| cagaacttta tgttttgag tggtaataaa acaattctcc tgtgagagag ctgttaccttt | | 1348 |
| gtctgttatc tgtattgcta tccttagaca tctgggggg tggaatgtat tctgattttg | | 1408 |
| cgttttacg taaaaaaaaa aaaaaaaaa | | 1437 |

<210> SEQ ID NO 2
<211> LENGTH: 355
<212> TYPE: PRT
<213> ORGANISM: Papaver somniferum

<400> SEQUENCE: 2

Met Asp Thr Ala Glu Glu Arg Leu Lys Gly Gln Ala Glu Ile Trp Glu
1        5         10         15

His Met Phe Ala Phe Val Asp Ser Met Ala Leu Lys Cys Ala Val Glu
        20         25         30

Leu Gly Ile Pro Asp Ile Ile Asn Ser His Gly Arg Pro Val Thr Ile
    35         40         45

Ser Glu Ile Val Asp Ser Leu Lys Thr Asn Thr Pro Ser Ser Ser Pro
50        55         60

Asn Ile Asp Tyr Leu Thr Arg Ile Met Arg Leu Leu Val His Lys Arg
65        70         75         80

Leu Phe Thr Ser Glu Leu His Gln Glu Ser Asn Gln Leu Leu Tyr Asn
        85         90         95

Leu Thr Arg Ser Ser Lys Trp Leu Leu Lys Asp Ser Lys Phe Asn Leu
        100        105        110

Ser Pro Leu Val Leu Trp Glu Thr Asn Pro Ile Leu Leu Lys Pro Trp
    115        120        125

Gln Tyr Leu Gly Lys Cys Ala Gln Glu Lys Ser Ser Pro Phe Glu Arg
    130        135        140

Ala His Gly Cys Glu Ile Trp Asp Leu Ala Leu Ala Asp Pro Lys Phe
145        150        155        160

Asn Asn Phe Leu Asn Gly Ala Met Gln Cys Ser Thr Thr Thr Ile Ile
        165        170        175

Asn Glu Met Leu Leu Glu Tyr Lys Asp Gly Phe Ser Gly Ile Ala Gly
        180        185        190

Ser Leu Val Asp Val Gly Gly Gly Thr Gly Ser Ile Ile Ala Glu Ile
    195        200        205

```
Val Lys Ala His Pro His Ile Gln Gly Ile Asn Phe Asp Leu Pro His
    210                 215                 220
Val Val Ala Thr Ala Ala Glu Phe Pro Gly Val Lys His Val Gly Gly
225                 230                 235                 240
Asp Met Phe Val Asp Ile Pro Glu Ala Asp Ala Val Ile Met Lys Trp
                245                 250                 255
Ile Leu His Asp Trp Ser Asp Glu Asp Cys Thr Ile Ile Leu Lys Asn
                260                 265                 270
Cys Tyr Arg Ala Ile Arg Lys Lys Asn Gly Lys Val Ile Ile Val
                275                 280                 285
Asp Cys Val Leu Arg Pro Asp Gly Asn Asp Leu Phe Asp Lys Met Gly
    290                 295                 300
Leu Ile Phe Asp Val Leu Met Met Ala His Thr Thr Ala Gly Lys Glu
305                 310                 315                 320
Arg Thr Glu Ala Glu Trp Lys Ile Leu Leu Asn Asn Ala Gly Phe Pro
                325                 330                 335
Arg Tyr Asn Val Ile Arg Thr Pro Ala Phe Pro Cys Ile Ile Glu Ala
                340                 345                 350
Phe Pro Glu
    355

<210> SEQ ID NO 3
<211> LENGTH: 346
<212> TYPE: PRT
<213> ORGANISM: Papaver somniferum

<400> SEQUENCE: 3

Met Glu Thr Val Ser Lys Ile Asp Gln Gln Asn Gln Ala Lys Ile Trp
1               5                   10                  15
Lys Gln Ile Tyr Gly Phe Ala Glu Ser Leu Val Leu Lys Cys Ala Val
                20                  25                  30
Gln Leu Glu Ile Ala Glu Thr Leu His Asn Asn Val Lys Pro Met Ser
            35                  40                  45
Leu Ser Glu Leu Ala Ser Lys Leu Pro Val Ala Gln Pro Val Asn Glu
        50                  55                  60
Asp Arg Leu Phe Arg Ile Met Arg Tyr Leu Val His Met Glu Leu Phe
65                  70                  75                  80
Lys Ile Asp Ala Thr Thr Gln Lys Tyr Ser Leu Ala Pro Pro Ala Lys
                85                  90                  95
Tyr Leu Leu Arg Gly Trp Glu Lys Ser Met Val Asp Ser Ile Leu Cys
                100                 105                 110
Ile Asn Asp Lys Asp Phe Leu Ala Pro Trp His His Leu Gly Asp Gly
            115                 120                 125
Leu Thr Gly Asn Cys Asp Ala Phe Glu Lys Ala Leu Gly Lys Ser Ile
    130                 135                 140
Trp Val Tyr Met Ser Val Asn Pro Glu Lys Asn Gln Leu Phe Asn Ala
145                 150                 155                 160
Ala Met Ala Cys Asp Thr Arg Leu Val Thr Ser Ala Leu Ala Asn Glu
                165                 170                 175
Cys Lys Ser Ile Phe Ser Asp Gly Ile Ser Thr Leu Val Asp Val Gly
                180                 185                 190
Gly Gly Thr Gly Thr Ala Val Lys Ala Ile Ser Lys Ala Phe Pro Asp
            195                 200                 205
Ile Lys Cys Thr Ile Tyr Asp Leu Pro His Val Ile Ala Asp Ser Pro
    210                 215                 220
```

```
Glu Ile Pro Asn Ile Thr Lys Ile Ser Gly Asp Met Phe Lys Ser Ile
225                 230                 235                 240

Pro Ser Ala Asp Ala Ile Phe Met Lys Cys Ile Leu His Asp Trp Asn
            245                 250                 255

Asp Asp Glu Cys Ile Gln Ile Leu Lys Arg Cys Lys Glu Ala Leu Pro
        260                 265                 270

Lys Gly Gly Lys Val Ile Val Asp Val Val Ile Asp Met Asp Ser
    275                 280                 285

Thr His Pro Tyr Ala Lys Ile Arg Leu Thr Leu Asp Leu Asp Met Met
    290                 295                 300

Leu Asn Thr Gly Gly Lys Glu Arg Thr Lys Glu Glu Trp Lys Thr Leu
305                 310                 315                 320

Phe Asp Ala Ala Gly Phe Ala Ser His Lys Val Thr Gln Ile Ser Ala
                325                 330                 335

Val Gln Ser Val Ile Glu Ala Tyr Pro Tyr
            340                 345

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
agtcatttcc atctggtcgc aaca                                        24

<210> SEQ ID NO 5
<211> LENGTH: 24
<212> TYPE: DNA
<213> ORGANISM: Artificial
<220> FEATURE:
<223> OTHER INFORMATION: primer

<400> SEQUENCE: 5
atggatactg cagaagaaag gttg                                        24

<210> SEQ ID NO 6
<211> LENGTH: 27
<212> TYPE: DNA
<213> ORGANISM: Artificial
<220> FEATURE:
<223> OTHER INFORMATION: primer

<400> SEQUENCE: 6
ataagggtaa gcctcaatta cagattg                                     27

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
gctgcagtga aagccataat ct                                          22

<210> SEQ ID NO 8
<211> LENGTH: 25
<212> TYPE: DNA
<213> ORGANISM: Artificial
<220> FEATURE:
```

```
<223> OTHER INFORMATION: primer

<400> SEQUENCE: 8
tatcggatcc atggatactg cagaa                                              25

<210> SEQ ID NO 9
<211> LENGTH: 27
<212> TYPE: DNA
<213> ORGANISM: Artificial
<220> FEATURE:
<223> OTHER INFORMATION: primer

<400> SEQUENCE: 9
ttaggcggcc gcttattctg gaaaggc                                            27

<210> SEQ ID NO 10
<211> LENGTH: 25
<212> TYPE: DNA
<213> ORGANISM: Artificial
<220> FEATURE:
<223> OTHER INFORMATION: primer

<400> SEQUENCE: 10
tatcggatcc atggaaacag taagc                                              25

<210> SEQ ID NO 11
<211> LENGTH: 27
<212> TYPE: DNA
<213> ORGANISM: Artificial
<220> FEATURE:
<223> OTHER INFORMATION: primer

<400> SEQUENCE: 11
ttaggcggcc gcttaataag ggtaagc                                            27

<210> SEQ ID NO 12
<211> LENGTH: 15
<212> TYPE: PRT
<213> ORGANISM: Papaver somniferum

<400> SEQUENCE: 12

Val Ile Ile Val Asp Cys Val Leu Arg Pro Asp Gly Asn Asp Leu
1               5                   10                  15

<210> SEQ ID NO 13
<211> LENGTH: 15
<212> TYPE: PRT
<213> ORGANISM: Papaver somniferum

<400> SEQUENCE: 13

Val Gly Gly Asp Met Phe Val Asp Ile Pro Glu Ala Asp Ala Val
1               5                   10                  15

<210> SEQ ID NO 14
<211> LENGTH: 25
<212> TYPE: PRT
<213> ORGANISM: Papaver somniferum

<400> SEQUENCE: 14

Ile Leu Leu Asn Asn Ala Gly Phe Pro Arg Tyr Asn Val Ile Arg Thr
1               5                   10                  15

Pro Ala Phe Pro Cys Ile Ile Glu Ala
            20                  25
```

-continued

<210> SEQ ID NO 15
<211> LENGTH: 14
<212> TYPE: PRT
<213> ORGANISM: Papaver somniferum

<400> SEQUENCE: 15

Asp Gly Phe Ser Gly Ile Ala Gly Ser Leu Val Asp Gly Gly
1               5                  10

<210> SEQ ID NO 16
<211> LENGTH: 26
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(24)
<223> OTHER INFORMATION: nuleotides 3, 6, 9, 12, 15, 21 and 24 are
      inosine

<400> SEQUENCE: 16
gcnggnwsny tngtngaygt nggngg                                          26

<210> SEQ ID NO 17
<211> LENGTH: 21
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (4)..(13)
<223> OTHER INFORMATION: nucleotides 4, 10 and 13 are inosine

<400> SEQUENCE: 17
ytcngcytcn gtnckytcct t                                               21

<210> SEQ ID NO 18
<211> LENGTH: 1346
<212> TYPE: DNA
<213> ORGANISM: Papaver somniferum
<220> FEATURE:
<221> NAME/KEY: misc_feature
<222> LOCATION: (731)..(731)
<223> OTHER INFORMATION: a, g, c ou t
<220> FEATURE:
<221> NAME/KEY: CDS
<222> LOCATION: (60)..(1100)
<223> OTHER INFORMATION:

<400> SEQUENCE: 18
gagctcaaat cattcaatca ttcttctcat caacagctaa agtgtctaaa cagagagaa      59 atg gaa aca gta agc aag att gat caa caa aac caa gca aaa atc tgg     107
Met Glu Thr Val Ser Lys Ile Asp Gln Gln Asn Gln Ala Lys Ile Trp
1               5                  10                  15 aaa caa att tac ggt ttc gca gaa tca cta gtt ctg aaa tgt gca gtc     155
Lys Gln Ile Tyr Gly Phe Ala Glu Ser Leu Val Leu Lys Cys Ala Val
                20                  25                  30 caa cta gag att gct gaa aca ctt cac aac aat gtc aaa ccc atg tct     203
Gln Leu Glu Ile Ala Glu Thr Leu His Asn Asn Val Lys Pro Met Ser
            35                  40                  45 tta tcc gaa ttg gca tcg aaa ctt ccc gtt gct caa ccc gtt aac gaa     251
Leu Ser Glu Leu Ala Ser Lys Leu Pro Val Ala Gln Pro Val Asn Glu
        50                  55                  60 gac cgt ctg ttc cga att atg cgt tac ttg gtt cac atg gag ctc ttc     299
Asp Arg Leu Phe Arg Ile Met Arg Tyr Leu Val His Met Glu Leu Phe

```
                65                  70                  75                  80
aaa ata gat gct acc acg cag aaa tac tca tta gct cca cca gct aag         347
Lys Ile Asp Ala Thr Thr Gln Lys Tyr Ser Leu Ala Pro Pro Ala Lys
                    85                  90                  95 tat ttg ttg aga ggc tgg gag aaa tca atg gtt gat tca att tta tgc         395
Tyr Leu Leu Arg Gly Trp Glu Lys Ser Met Val Asp Ser Ile Leu Cys
                100                 105                 110 ata aat gat aag gat ttc tta gct cca tgg cac cat tta ggc gac ggt         443
Ile Asn Asp Lys Asp Phe Leu Ala Pro Trp His His Leu Gly Asp Gly
                115                 120                 125 ttg acc ggt aac tgt gac gct ttt gag aaa gcg ttg ggg aag agt att         491
Leu Thr Gly Asn Cys Asp Ala Phe Glu Lys Ala Leu Gly Lys Ser Ile
            130                 135                 140 tgg gtg tat atg agt gta aat cct gaa aag aat caa ttg ttt aat gca         539
Trp Val Tyr Met Ser Val Asn Pro Glu Lys Asn Gln Leu Phe Asn Ala
145                 150                 155                 160 gca atg gct tgt gat act aga ttg gtt act tct gca ttg gct aat gag         587
Ala Met Ala Cys Asp Thr Arg Leu Val Thr Ser Ala Leu Ala Asn Glu
                165                 170                 175 tgc aaa agt att ttc agt gat gga atc agt aca ctg gtt gat gtc ggc         635
Cys Lys Ser Ile Phe Ser Asp Gly Ile Ser Thr Leu Val Asp Val Gly
                180                 185                 190 ggt ggt acg ggt act gca gtg aaa gcc ata tct aaa gct ttt ccg gat         683
Gly Gly Thr Gly Thr Ala Val Lys Ala Ile Ser Lys Ala Phe Pro Asp
            195                 200                 205 att aag tgc act atc tat gat ctt cct cat gtc ata gct gat tct ccn         731
Ile Lys Cys Thr Ile Tyr Asp Leu Pro His Val Ile Ala Asp Ser Pro
210                 215                 220 gaa atc ccc aat atc act aaa att tct gga gat atg ttc aag tct att         779
Glu Ile Pro Asn Ile Thr Lys Ile Ser Gly Asp Met Phe Lys Ser Ile
225                 230                 235                 240 cct agt gct gat gcc atc ttc atg aag tgc ata ctt cac gac tgg aac         827
Pro Ser Ala Asp Ala Ile Phe Met Lys Cys Ile Leu His Asp Trp Asn
                245                 250                 255 gat gac gaa tgc att caa atc ttg aag aga tgc aaa gaa gca tta cca         875
Asp Asp Glu Cys Ile Gln Ile Leu Lys Arg Cys Lys Glu Ala Leu Pro
                260                 265                 270 aaa ggt ggc aaa gtt att atc gtg gat gtc gtg ata gac atg gat tcg         923
Lys Gly Gly Lys Val Ile Ile Val Asp Val Val Ile Asp Met Asp Ser
            275                 280                 285 act cat cca tat gca aaa att aga ctc aca ctg gat ttg gat atg atg         971
Thr His Pro Tyr Ala Lys Ile Arg Leu Thr Leu Asp Leu Asp Met Met
            290                 295                 300 ctt aac act ggt gga aaa gag aga acc aaa gaa gaa tgg aag aca ctt         1019
Leu Asn Thr Gly Gly Lys Glu Arg Thr Lys Glu Glu Trp Lys Thr Leu
305                 310                 315                 320 ttt gat gcc gct ggt ttt gct agc cac aaa gtc act cag ata tct gct         1067
Phe Asp Ala Ala Gly Phe Ala Ser His Lys Val Thr Gln Ile Ser Ala
                325                 330                 335 gtc caa tct gta att gag gct tac cct tat taa ggaacatttt aaccggtttt      1120
Val Gln Ser Val Ile Glu Ala Tyr Pro Tyr
            340                 345 ccctttgatt aattgttgct ttctctttgg attatgttta tgtttataac aattgcaaga      1180
tgaatgactt ccaactcgca ttggattaat gttttcgtt tacttactt tctagatatt       1240 ttgaggggct tgtttaaat ttgatatccc acgtttgtaa ctgtaaagag tagagtggat      1300
gaatgatact ccctccgttt ccaaaaaaaa aaaaaaaaa aaaaaa                      1346
```

<210> SEQ ID NO 19
<211> LENGTH: 346
<212> TYPE: PRT
<213> ORGANISM: Papaver somniferum

<400> SEQUENCE: 19

```
Met Glu Thr Val Ser Lys Ile Asp Gln Gln Asn Gln Ala Lys Ile Trp
1               5                   10                  15
Lys Gln Ile Tyr Gly Phe Ala Glu Ser Leu Val Leu Lys Cys Ala Val
                20                  25                  30
Gln Leu Glu Ile Ala Glu Thr Leu His Asn Asn Val Lys Pro Met Ser
            35                  40                  45
Leu Ser Glu Leu Ala Ser Lys Leu Pro Val Ala Gln Pro Val Asn Glu
        50                  55                  60
Asp Arg Leu Phe Arg Ile Met Arg Tyr Leu Val His Met Glu Leu Phe
65                  70                  75                  80
Lys Ile Asp Ala Thr Thr Gln Lys Tyr Ser Leu Ala Pro Pro Ala Lys
                85                  90                  95
Tyr Leu Leu Arg Gly Trp Glu Lys Ser Met Val Asp Ser Ile Leu Cys
            100                 105                 110
Ile Asn Asp Lys Asp Phe Leu Ala Pro Trp His His Leu Gly Asp Gly
        115                 120                 125
Leu Thr Gly Asn Cys Asp Ala Phe Glu Lys Ala Leu Gly Lys Ser Ile
130                 135                 140
Trp Val Tyr Met Ser Val Asn Pro Glu Lys Asn Gln Leu Phe Asn Ala
145                 150                 155                 160
Ala Met Ala Cys Asp Thr Arg Leu Val Thr Ser Ala Leu Ala Asn Glu
                165                 170                 175
Cys Lys Ser Ile Phe Ser Asp Gly Ile Ser Thr Leu Val Asp Val Gly
            180                 185                 190
Gly Gly Thr Gly Thr Ala Val Lys Ala Ile Ser Lys Ala Phe Pro Asp
        195                 200                 205
Ile Lys Cys Thr Ile Tyr Asp Leu Pro His Val Ile Ala Asp Ser Pro
210                 215                 220
Glu Ile Pro Asn Ile Thr Lys Ile Ser Gly Asp Met Phe Lys Ser Ile
225                 230                 235                 240
Pro Ser Ala Asp Ala Ile Phe Met Lys Cys Ile Leu His Asp Trp Asn
                245                 250                 255
Asp Asp Glu Cys Ile Gln Ile Leu Lys Arg Cys Lys Glu Ala Leu Pro
            260                 265                 270
Lys Gly Gly Lys Val Ile Ile Val Asp Val Val Ile Asp Met Asp Ser
        275                 280                 285
Thr His Pro Tyr Ala Lys Ile Arg Leu Thr Leu Asp Leu Asp Met Met
290                 295                 300
Leu Asn Thr Gly Gly Lys Glu Arg Thr Lys Glu Glu Trp Lys Thr Leu
305                 310                 315                 320
Phe Asp Ala Ala Gly Phe Ala Ser His Lys Val Thr Gln Ile Ser Ala
                325                 330                 335
Val Gln Ser Val Ile Glu Ala Tyr Pro Tyr
            340                 345
```

<210> SEQ ID NO 20
<211> LENGTH: 1041
<212> TYPE: DNA
<213> ORGANISM: Papaver somniferum
<220> FEATURE:

<220> NAME/KEY: CDS
<222> LOCATION: (1)..(1041)
<223> OTHER INFORMATION:

<400> SEQUENCE: 20

```
atg gaa aca gta agc aag att gat caa caa aac caa gca aaa atc tgg      48
Met Glu Thr Val Ser Lys Ile Asp Gln Gln Asn Gln Ala Lys Ile Trp
1               5                  10                  15 aaa caa att tac ggt ttc gca gaa tca cta gtt ctg aaa tgt gca gtc      96
Lys Gln Ile Tyr Gly Phe Ala Glu Ser Leu Val Leu Lys Cys Ala Val
            20                  25                  30 caa cta gag att gct gaa aca ctt cac aac aat gtc aaa ccc atg tct     144
Gln Leu Glu Ile Ala Glu Thr Leu His Asn Asn Val Lys Pro Met Ser
        35                  40                  45 tta tcc gaa ttg gca tcg aaa ctt ccc gtt gct caa ccc gtt aac gaa     192
Leu Ser Glu Leu Ala Ser Lys Leu Pro Val Ala Gln Pro Val Asn Glu
    50                  55                  60 gac cgt ctg ttc cga att atg cgt tac ttg gtt cac atg gag ctc ttc     240
Asp Arg Leu Phe Arg Ile Met Arg Tyr Leu Val His Met Glu Leu Phe
65                  70                  75                  80 aaa ata gat gct acc acg cag aaa tac tca tta gtt cca cca gct aag     288
Lys Ile Asp Ala Thr Thr Gln Lys Tyr Ser Leu Val Pro Pro Ala Lys
                85                  90                  95 tat ttg ttg aga ggc tgg gag aaa tca atg gtt gat tca att tta tgc     336
Tyr Leu Leu Arg Gly Trp Glu Lys Ser Met Val Asp Ser Ile Leu Cys
            100                 105                 110 ata aat gat aag gat ttc tta gct cca tgg cac cat tta ggc gac ggt     384
Ile Asn Asp Lys Asp Phe Leu Ala Pro Trp His His Leu Gly Asp Gly
        115                 120                 125 ttg acc ggt aac tgt gac gct ttt gag aaa gcg ttg ggg aag agt att     432
Leu Thr Gly Asn Cys Asp Ala Phe Glu Lys Ala Leu Gly Lys Ser Ile
    130                 135                 140 tgg gtg tat atg agt gaa aat cct gaa aag aat caa ttg ttt aat gca     480
Trp Val Tyr Met Ser Glu Asn Pro Glu Lys Asn Gln Leu Phe Asn Ala
145                 150                 155                 160 gca atg gct tgt gat act aga ttg gtt act tct gca ttg gct aat gag     528
Ala Met Ala Cys Asp Thr Arg Leu Val Thr Ser Ala Leu Ala Asn Glu
                165                 170                 175 tgc aaa agt att ttc agt gat gga atc agt aca ctg gtt gat gtc ggc     576
Cys Lys Ser Ile Phe Ser Asp Gly Ile Ser Thr Leu Val Asp Val Gly
            180                 185                 190 ggt ggt acg ggt act gca gtg aaa gcc ata tct aaa gct ttt ccg gat     624
Gly Gly Thr Gly Thr Ala Val Lys Ala Ile Ser Lys Ala Phe Pro Asp
        195                 200                 205 att aag tgc act atc tat gat ctt cct cat gtc ata gct gat tct cct     672
Ile Lys Cys Thr Ile Tyr Asp Leu Pro His Val Ile Ala Asp Ser Pro
    210                 215                 220 gaa atc ccc aat atc act aaa att cct gga gat atg ttc aag tct att     720
Glu Ile Pro Asn Ile Thr Lys Ile Pro Gly Asp Met Phe Lys Ser Ile
225                 230                 235                 240 cct agt gct gat ggc atc ttc atg aag tgc ata ctt cac gac tgg aac     768
Pro Ser Ala Asp Gly Ile Phe Met Lys Cys Ile Leu His Asp Trp Asn
                245                 250                 255 gat gac gaa tgc att caa atc ttg aag aga tgc aaa gaa gca tta cca     816
Asp Asp Glu Cys Ile Gln Ile Leu Lys Arg Cys Lys Glu Ala Leu Pro
            260                 265                 270 aaa gtt ggc aaa gtt att atc gtg gat gtc gtg ata gac atg gat tcg     864
Lys Val Gly Lys Val Ile Ile Val Asp Val Val Ile Asp Met Asp Ser
        275                 280                 285 act cat cca tat gca aaa att aga ctc aca ctg gat ttg gat atg atg     912
```

```
Thr His Pro Tyr Ala Lys Ile Arg Leu Thr Leu Asp Leu Asp Met Met
    290                 295                 300 ctt aac act ggt gga aaa gag aga acc aaa gaa gaa tgg aag aca ctt     960
Leu Asn Thr Gly Gly Lys Glu Arg Thr Lys Glu Glu Trp Lys Thr Leu
305                 310                 315                 320 ttt gat gcc gct ggt ttt gct agc cac aaa gtc act cag ata tct gct    1008
Phe Asp Ala Ala Gly Phe Ala Ser His Lys Val Thr Gln Ile Ser Ala
                325                 330                 335 gtc caa tct gta att gag gct tac cct tat taa                         1041
Val Gln Ser Val Ile Glu Ala Tyr Pro Tyr
                340                 345

<210> SEQ ID NO 21
<211> LENGTH: 346
<212> TYPE: PRT
<213> ORGANISM: Papaver somniferum

<400> SEQUENCE: 21

Met Glu Thr Val Ser Lys Ile Asp Gln Gln Asn Gln Ala Lys Ile Trp
1               5                   10                  15

Lys Gln Ile Tyr Gly Phe Ala Glu Ser Leu Val Leu Lys Cys Ala Val
            20                  25                  30

Gln Leu Glu Ile Ala Glu Thr Leu His Asn Asn Val Lys Pro Met Ser
        35                  40                  45

Leu Ser Glu Leu Ala Ser Lys Leu Pro Val Ala Gln Pro Val Asn Glu
    50                  55                  60

Asp Arg Leu Phe Arg Ile Met Arg Tyr Leu Val His Met Glu Leu Phe
65                  70                  75                  80

Lys Ile Asp Ala Thr Thr Gln Lys Tyr Ser Leu Val Pro Pro Ala Lys
                85                  90                  95

Tyr Leu Leu Arg Gly Trp Glu Lys Ser Met Val Asp Ser Ile Leu Cys
            100                 105                 110

Ile Asn Asp Lys Asp Phe Leu Ala Pro Trp His His Leu Gly Asp Gly
        115                 120                 125

Leu Thr Gly Asn Cys Asp Ala Phe Glu Lys Ala Leu Gly Lys Ser Ile
    130                 135                 140

Trp Val Tyr Met Ser Glu Asn Pro Glu Lys Asn Gln Leu Phe Asn Ala
145                 150                 155                 160

Ala Met Ala Cys Asp Thr Arg Leu Val Thr Ser Ala Leu Ala Asn Glu
                165                 170                 175

Cys Lys Ser Ile Phe Ser Asp Gly Ile Ser Thr Leu Val Asp Val Gly
            180                 185                 190

Gly Gly Thr Gly Thr Ala Val Lys Ala Ile Ser Lys Ala Phe Pro Asp
        195                 200                 205

Ile Lys Cys Thr Ile Tyr Asp Leu Pro His Val Ile Ala Asp Ser Pro
    210                 215                 220

Glu Ile Pro Asn Ile Thr Lys Ile Pro Gly Asp Met Phe Lys Ser Ile
225                 230                 235                 240

Pro Ser Ala Asp Gly Ile Phe Met Lys Cys Ile Leu His Asp Trp Asn
                245                 250                 255

Asp Asp Glu Cys Ile Gln Ile Leu Lys Arg Cys Lys Glu Ala Leu Pro
            260                 265                 270

Lys Val Gly Lys Val Ile Ile Val Asp Val Val Ile Asp Met Asp Ser
        275                 280                 285

Thr His Pro Tyr Ala Lys Ile Arg Leu Thr Leu Asp Leu Asp Met Met
    290                 295                 300
```

-continued

```
Leu Asn Thr Gly Gly Lys Glu Arg Thr Lys Glu Glu Trp Lys Thr Leu
305                 310                 315                 320

Phe Asp Ala Ala Gly Phe Ala Ser His Lys Val Thr Gln Ile Ser Ala
            325                 330                 335

Val Gln Ser Val Ile Glu Ala Tyr Pro Tyr
            340                 345

<210> SEQ ID NO 22
<211> LENGTH: 1194
<212> TYPE: DNA
<213> ORGANISM: Papaver somniferum
<220> FEATURE:
<221> NAME/KEY: CDS
<222> LOCATION: (28)..(1068)
<223> OTHER INFORMATION:

<400> SEQUENCE: 22
gcagctaaag tgtctaaaca gagagaa atg gaa aca gta agc aag att gat caa    54
                            Met Glu Thr Val Ser Lys Ile Asp Gln
                              1               5 caa aac caa gca aaa atc tgg aaa caa att tac ggt ttc gca gaa tca    102
Gln Asn Gln Ala Lys Ile Trp Lys Gln Ile Tyr Gly Phe Ala Glu Ser
 10                  15                  20                  25 cta gtt ctg aaa tgt gca gtc caa cta gag att gct gaa aca ctt cac    150
Leu Val Leu Lys Cys Ala Val Gln Leu Glu Ile Ala Glu Thr Leu His
                 30                  35                  40 aac aat gtc aaa ccc atg tct tta tcc gaa ttg gca tcg aaa ctt ccc    198
Asn Asn Val Lys Pro Met Ser Leu Ser Glu Leu Ala Ser Lys Leu Pro
             45                  50                  55 gtt gct caa ccc gtt aac gaa gac cgt ctg ttc cga att atg cgt tac    246
Val Ala Gln Pro Val Asn Glu Asp Arg Leu Phe Arg Ile Met Arg Tyr
         60                  65                  70 ttg gtt cac atg gag ctc ttc aaa ata gat gct acc acg cag aaa tac    294
Leu Val His Met Glu Leu Phe Lys Ile Asp Ala Thr Thr Gln Lys Tyr
     75                  80                  85 tca tta gct cca cca gct aag tat ttg ttg aga ggc tgg gag aaa tca    342
Ser Leu Ala Pro Pro Ala Lys Tyr Leu Leu Arg Gly Trp Glu Lys Ser
 90                  95                 100                 105 atg gtt gat tca att tta tgc ata aat gat aag gat ttc tta gct cca    390
Met Val Asp Ser Ile Leu Cys Ile Asn Asp Lys Asp Phe Leu Ala Pro
                110                 115                 120 tgg cac cat tta ggc gac ggt ttg acc ggt aac tgt gac gct ttt gag    438
Trp His His Leu Gly Asp Gly Leu Thr Gly Asn Cys Asp Ala Phe Glu
            125                 130                 135 aaa gcg ttg ggg aag agt att tgg gtg tat atg agt gaa aat cct gaa    486
Lys Ala Leu Gly Lys Ser Ile Trp Val Tyr Met Ser Glu Asn Pro Glu
        140                 145                 150 aag aat caa ttg ttt aat gca gca atg gct tgt gat act aga ttg gtt    534
Lys Asn Gln Leu Phe Asn Ala Ala Met Ala Cys Asp Thr Arg Leu Val
    155                 160                 165 act tct gca ttg gct aat gag tgc aaa agt att ttc agt gat gga atc    582
Thr Ser Ala Leu Ala Asn Glu Cys Lys Ser Ile Phe Ser Asp Gly Ile
170                 175                 180                 185 agt aca ctg gtt gat gtc ggc ggt ggt acg ggt act gca gtg aaa gcc    630
Ser Thr Leu Val Asp Val Gly Gly Gly Thr Gly Thr Ala Val Lys Ala
                190                 195                 200 ata tct aaa gct ttt ccg gat att aag tgc act atc tat gat ctt cct    678
Ile Ser Lys Ala Phe Pro Asp Ile Lys Cys Thr Ile Tyr Asp Leu Pro
            205                 210                 215 cat gtc ata gct gat tct cct gaa atc ccc aat atc act aaa att tct    726
```

```
His Val Ile Ala Asp Ser Pro Glu Ile Pro Asn Ile Thr Lys Ile Ser
        220                 225                 230 gga gat atg ttc aag tct att cct agt gct gat gcc atc ttc atg aag    774
Gly Asp Met Phe Lys Ser Ile Pro Ser Ala Asp Ala Ile Phe Met Lys
235                 240                 245 tgc ata ctt cac gac tgg aac gat gat gaa tgc att caa atc ttg aag    822
Cys Ile Leu His Asp Trp Asn Asp Asp Glu Cys Ile Gln Ile Leu Lys
250                 255                 260                 265 aga tgc aaa gaa gca tta cca aaa gtt ggc aaa gtt att atc gtg gat    870
Arg Cys Lys Glu Ala Leu Pro Lys Val Gly Lys Val Ile Ile Val Asp
                270                 275                 280 gtc gtg ata gac atg gat tcg act cat cca tat gca aaa att aga ctc    918
Val Val Ile Asp Met Asp Ser Thr His Pro Tyr Ala Lys Ile Arg Leu
            285                 290                 295 aca ctg gat ttg gat atg atg ctt aac act ggt gga aaa gag aga acc    966
Thr Leu Asp Leu Asp Met Met Leu Asn Thr Gly Gly Lys Glu Arg Thr
        300                 305                 310 aaa gaa gaa tgg aag aca ctt ttt gat gcc gct ggt ttt gct agc cac   1014
Lys Glu Glu Trp Lys Thr Leu Phe Asp Ala Ala Gly Phe Ala Ser His
315                 320                 325 aaa gtc act cag ata tct gct gtc caa tct gta att gag gct tac cct   1062
Lys Val Thr Gln Ile Ser Ala Val Gln Ser Val Ile Glu Ala Tyr Pro
330                 335                 340                 345 tat taa ggaacatttt aaccggtttt ccctttgatt aattgttgct ttctctttgg    1118
Tyr attatgttta tgtttataac aattgcaaga tgaatgaatt tccaacttgc attggattaa  1178
aaaaaaaaaa aaaaaa                                                  1194

<210> SEQ ID NO 23
<211> LENGTH: 346
<212> TYPE: PRT
<213> ORGANISM: Papaver somniferum

<400> SEQUENCE: 23

Met Glu Thr Val Ser Lys Ile Asp Gln Gln Asn Gln Ala Lys Ile Trp
1               5                   10                  15

Lys Gln Ile Tyr Gly Phe Ala Glu Ser Leu Val Leu Lys Cys Ala Val
                20                  25                  30

Gln Leu Glu Ile Ala Glu Thr Leu His Asn Asn Val Lys Pro Met Ser
            35                  40                  45

Leu Ser Glu Leu Ala Ser Lys Leu Pro Val Ala Gln Pro Val Asn Glu
        50                  55                  60

Asp Arg Leu Phe Arg Ile Met Arg Tyr Leu Val His Met Glu Leu Phe
65                  70                  75                  80

Lys Ile Asp Ala Thr Thr Gln Lys Tyr Ser Leu Ala Pro Pro Ala Lys
                85                  90                  95

Tyr Leu Leu Arg Gly Trp Glu Lys Ser Met Val Asp Ser Ile Leu Cys
            100                 105                 110

Ile Asn Asp Lys Asp Phe Leu Ala Pro Trp His His Leu Gly Asp Gly
        115                 120                 125

Leu Thr Gly Asn Cys Asp Ala Phe Glu Lys Ala Leu Gly Lys Ser Ile
    130                 135                 140

Trp Val Tyr Met Ser Glu Asn Pro Glu Lys Asn Gln Leu Phe Asn Ala
145                 150                 155                 160

Ala Met Ala Cys Asp Thr Arg Leu Val Thr Ser Ala Leu Ala Asn Glu
                165                 170                 175
```

-continued

```
Cys Lys Ser Ile Phe Ser Asp Gly Ile Ser Thr Leu Val Asp Val Gly
        180                 185                 190

Gly Gly Thr Gly Thr Ala Val Lys Ala Ile Ser Lys Ala Phe Pro Asp
        195                 200                 205

Ile Lys Cys Thr Ile Tyr Asp Leu Pro His Val Ile Ala Asp Ser Pro
    210                 215                 220

Glu Ile Pro Asn Ile Thr Lys Ile Ser Gly Asp Met Phe Lys Ser Ile
225                 230                 235                 240

Pro Ser Ala Asp Ala Ile Phe Met Lys Cys Ile Leu His Asp Trp Asn
            245                 250                 255

Asp Asp Glu Cys Ile Gln Ile Leu Lys Arg Cys Lys Glu Ala Leu Pro
            260                 265                 270

Lys Val Gly Lys Val Ile Ile Val Asp Val Val Ile Asp Met Asp Ser
        275                 280                 285

Thr His Pro Tyr Ala Lys Ile Arg Leu Thr Leu Asp Leu Asp Met Met
        290                 295                 300

Leu Asn Thr Gly Gly Lys Glu Arg Thr Lys Glu Glu Trp Lys Thr Leu
305                 310                 315                 320

Phe Asp Ala Ala Gly Phe Ala Ser His Lys Val Thr Gln Ile Ser Ala
                325                 330                 335

Val Gln Ser Val Ile Glu Ala Tyr Pro Tyr
            340                 345

<210> SEQ ID NO 24
<211> LENGTH: 5
<212> TYPE: PRT
<213> ORGANISM: Papaver somniferum

<400> SEQUENCE: 24

Arg Thr Glu Ala Glu
1               5
```

O-METHYLTRANSFERASES OF TETRAHYDROBENZYLISOQUINOLINE ALKALOID BIOSYNTHESIS IN *PAPAVER SOMNIFERUM*

The present invention relates to methyl transfer enzymes involved in alkaloid biosynthesis in opium poppy. More particularly, the invention relates to proteins having (R,S)-reticuline 7-O-methyltransferase activity, to proteins having (R,S)-norcoclaurine 6-O-methyltransferase activity and to derivatives and analogues of these proteins. The invention also relates to nucleic acid molecules encoding the proteins, and their derivatives and analogues, and to their use in the production of methylated catechols and tetrahydrobenzylisoquinolines.

Enzymatic methylation is a ubiquitous reaction occurring in diverse organisms including bacteria, fungi, plants and animals, and resulting in the modification of acceptor molecules for different functional and regulatory purposes. Enzymatic O-methylation is catalyzed by O-methyltransferases [E.C.2.1.1.6.x], and involves the transfer of the methyl group of S-adenosyl-L-methionine (AdoMet) to the hydroxyl group of an acceptor molecule. S-Adenosylmethionine (AdoMet)[1]-dependent O-methyltransferases (OMTs) are important components of plant natural product biosynthesis, yielding methyl ether derivatives of hydroxylated polycyclic aromatic low molecular weight compounds. Regiospecific oxygen methylation significantly contributes to the vast metabolic diversity of plant secondary metabolism.

Over the past few years, the structural genes of several plant OMTs have been isolated, often using homology-based cloning techniques which exploit the high amino acid sequence similarity observed between plant OMTs, and the presence of conserved sequence motifs (Refs 1-3). However, whilst amino acid sequence comparison can assist in the isolation of the genes, it cannot be used to reliably predict the in vivo function of plant OMTs because of the broad substrate specificities that can be found for closely related enzymes. Indeed, it has become clear that substrate discrimination by plant O-methyltransferases can vary among the same enzyme from different species, for example the different substrate specificity of coclaurine 6-O-methyltransferase of tetrahydrobenzylisoquinoline alkaloid biosynthesis from *Thalictrum tuberosum* (4) and from *Coptis japonica* (5). This can also occur within one species, as for caffeic acid 3-O-methyltransferase from *Nicotiana tabacum* (6). In addition, many metabolic pathways in plants are only putatively elucidated, further complicating the assignment of a function to an isolated OMT gene. Fuctional characterisation of the enzymes is thus not trivial.

O-Methyltransferases of phenylpropanoid and of alkaloid biosynthesis are probably the biochemically best studied in the plant natural product field. They play a particularly important role in the opium poppy, *Papaver somniferum*, which produces more than eighty tetrahydrobenzylisoquinoline-derived alkaloids, including the narcotic analgesic phenanthrene alkaloids codeine and morphine, and the antitussive phthalidisoquinoline noscapine, the vasodilator papaverine and the antimicrobial benzo[c]phenanthridine sanguinarine.

As shown in FIG. 1, in *Papaver somniferum* a central biosynthetic pathway leads from two molecules of L-tyrosine to (S)-reticuline (reviewed in 7). The pathway then bifurcates as the (S)-reticuline molecule is regio- and stereospecifically transformed into committed isoquinoline subclass intermediates. Two classes of enzyme effectuate this diversification—oxidoreductases and O-methyltransferases. The latter enzymes catalyze two steps in the formation of (S)-reticuline, prior to the branch point of the morphine and sanguinarine pathways. Then in the specific pathway that leads to morphine, (S)-reticuline is oxidized by (S)-reticuline oxidase to form the dehydroreticulinium ion, which is then stereospecifically reduced to (R)-reticuline. To enter the sanguinarine pathway, the N-methyl group of (S)-reticuline is oxidatively cyclized by the berberine bridge enzyme to the bridge carbon (C-8) of (S)-scoulerine.

Requisite to metabolic engineering of commercial varieties of *P. somniferum* is the understanding of the alkaloid biosynthetic pathways at the molecular genetic level. However, of the enzymes involved in alkaloid biosynthesis in *P. somniferum*, genes encoding only six of them have been isolated to date. One of the first to be isolated was a cDNA encoding the cytochrome P-450-dependent monooxygenase (S)-N-methylcoclaurine 3'-hydroxylase (8,9) and the corresponding cytochrome P-450 reductase (10). This enzyme is common to the biosynthetic pathways of all the *P. somniferum* alkaloids. Specific to the sanguinarine pathway is the cDNA encoding the berberine bridge enzyme (9,11,12). Finally, specific to morphine biosynthesis are the cDNAs for salutaridinol 7-O-acetyltransferase (13) that results in the formation of the five-ring system of the morphinans and for codeinone reductase, the penultimate enzyme of the morphine pathway that reduces codeinone to codeine (14).

With regard to the O-methyl transferases involved in *P. somniferum* alkaloid biosynthesis, very little is known to date. Norcoclaurine 6-O-methyltransferase activity and (S)-3'-hydroxy-N-methylcoclaurine 4'-O-methyltransferase activity have been detected in protein extracts of *P. somniferum* (29). Recently, Facchini and Park published the mRNA and amino acid sequence of a putative norcoclaurine 6-O-methyltransferase from *P. somniferum* (31) However the function of the enzyme was not investigated by these authors. Decker (30) carried out a study aimed at characterizing proteins in the latex of *P. somniferum* using two-dimensional gel electrophoresis, and demonstrated the presence of spots, which, once excised and micro-sequenced were seen to have homology with a maize O-methyl transferase. To date, however, no O-methyl transferases involved in *P. somniferum* alkaloid biosynthesis have been cloned and fully characterised. Moreover, to date no reports of (R,S)-reticuline 7-O-methyltransferase activity in *P. somniferum* have ever been made in the literature.

It is thus an object of the present invention to identify and characterise both at the protein and nucleic acid levels, and at the functional level, O-methyl transferases involved in *P. somniferum* alkaloid biosynthesis.

More specifically, the present invention relates to the isolation and characterization of cDNAs encoding O-methyltransferases of tetrahydrobenzylisoquinoline alkaloid biosynthesis in *P. somniferum*, namely (R,S)-reticuline 7-O-methyltransferase and (R,S)-norcoclaurine 6-O-methyltransferase.

In the framework of the present invention, the inventors have isolated S-Adenosyl-L-methionine:(R,S)-reticuline 7-O-methyltransferase, which converts reticuline to laudanine in tetrahydrobenzylisoquinoline biosynthesis in *Papaver somniferum*. A proteomic analysis of *P. somniferum* latex indicated the presence of protein(s) showing homology to a maize O-methyltransferase (30), but gave no indication as to whether the fragments were from a single protein, and no indication of the possible function of the protein. The cDNA was amplified from *P. somniferum* RNA by reverse transcription PCR using primers based on the internal amino acid sequences. The recombinant protein was expressed in *Spodoptera frugiperda* Sf9 cells in a baculovirus expression vector. Steady state kinetic measurements with the heterologously expressed enzyme and mass spectrometric analysis of the enzymic products suggest that the enzyme is capable of carry through sequential O-methylations, first on the isoquinoline-, then on the benzyl moiety of several substrates. The tetrahydrobenzylisoquinolines (R)-reticuline (4.20 s$^{-1}$ mM$^{-1}$), (S)-reticuline (4.50), (R)-protosinomenine (1.67), and (R,S)-isoorientaline (1.44) as well as guaiacol (5.87) and isovanillic acid (1.21) are O-methylated by the enzyme with the ratio k$_{cat}$/K$_m$ shown in parentheses. A phylogenetic comparison of the amino acid sequence of this O-methyltransferase to those from forty-three other plant species suggests that this enzyme groups more closely to isoquinoline biosynthetic O-methyltransferases from *Coptis japonica* than to those from *Thalictrum tuberosum*. In addition, *P. somniferum* cDNAs encoding two (R,S)-norcoclaurine 6-O-methyltransferases have been isolated and similarly characterized. The present inventors have thus surprisingly discovered that different alleles of (R,S)-norcoclaurine 6-O-methyltransferase exist in *P. somniferum*.

More specifically, the invention concerns a first protein, comprising or consisting of the *Papaver somniferum* (R,S)-reticuline 7-O-methyltransferase protein illustrated in FIG. 9 (SEQ. ID NO: 2), (hereafter designated the PSOMT1 sequence), or fragments or variants of the illustrated PSOMT1 sequence. The PSOMT1 proteins of the invention thus comprise or consist of:

i) the amino acid sequence illustrated in FIG. 9 (SEQ. ID NO: 2) ("PSOMT1") or, ii) a fragment of the amino acid sequence illustrated in FIG. 9 (SEQ. ID NO: 2), said fragment having at least 100 amino acids ("i.e. fragments of PSOMT1"), or iii) a variant of the amino acid sequence of FIG. 9 (SEQ. ID NO: 2), said variant having at least 70% identity with the amino acid sequence of FIG. 9 (SEQ. ID NO: 2) over a length of at least 300 amino acids (i.e. "variants of PSOMT1").

The fragments or variants of the PSOMT1 protein as defined above will be collectively referred to herein as the "PSOMT1 derivatives".

Preferably, the PSOMT1 protein and derivatives are in dimeric form, i.e. the protein is a dimer comprising two protein sub-units, each sub-unit being chosen from any one of proteins (i), (ii) or (iii) as defined above. Both homodimers and heterodimers are within the scope of the invention. In the context of the invention, the designation "PSOMT1 proteins" includes dimeric forms of said proteins. The proteins may be purified from natural sources, or made by chemical or recombinant techniques.

According to the invention, the PSOMT1 protein and derivatives, and dimers thereof, generally have O-methyltransferase activity, particularly (R,S)-reticuline 7-O-methyltransferase activity. In the context of the invention, "(R,S)-reticuline 7-O-methyltransferase activity" signifies the capacity of a protein to methylate (R) or (S) or (R,S)-reticuline at the 7-hydroxyl group, forming (R)-7-O-methylreticuline, (S)-7-O-methylreticuline, and (R,S)-7-O-methylreticuline, respectively. The proteins of the invention catalyse this reaction both in vivo and in vitro. Preferably, the enzymes of the invention methylate (R) or (S)-reticuline with equal efficiency, as shown by substantially equal k$_{cat}$/K$_m$ ratios. The 7-O-methylation by PSOMT1 and derivatives preferably has a pH optimum of approximately pH 8.0, and a temperature optimum of 37° C. The (R,S)-reticuline 7-O-methyltransferase activity in vitro is measured using the experimental protocols described in the Examples below on purified enzyme as obtained from a eukaryotic cell, for example further to heterologous expression in a eukaryotic host, or any other suitable technique.

The PSOMT1 protein of the invention also has the capacity to methylate substrates other than (R) and (S)-reticuline. In particular, the PSOMT1 protein has the capacity to methylate in vitro the following substrates, in addition to (R)-reticuline, (S)-reticuline, at the 7-hydroxy position: guaiacol, isovanillic acid, (R,S)-orientaline, (R)-protosinomenine and (R,S)-isoorientaline. Optimal pH for these methylations are isovanillic acid: pH 7.5: (R)-protosinomenine pH 9.0; guaiacol: pH 8.0; (R,S)-isoorientaline: pH 7.5-9.0.

The PSOMT1 protein derivatives of the invention may also exhibit this capacity to methylate the above substrates in vitro.

A first preferred embodiment of the invention thus comprises the full length PSOMT1 (R,S)-reticuline 7-O-methyltransferase protein whose amino acid sequence is shown in FIG. 9 (PSOMT1) (SEQ. ID NO: 2). The protein of the invention as illustrated in FIG. 9 has 355 amino acids, and a molecular weight of approximately 43 kDa (Genebank accession number AY268893). According to this embodiment of the invention, the full length *P. somniferum* enzyme may be obtained by isolation and purification to homogeneity from cell suspension culture, or from plant parts of *P. somniferum*, at any stage of development, and from latex of mature or immature plants. Alternatively, the enzyme may be produced by recombinant means in suitable host cells such as plant cells or insect cells. The protein may consist exclusively of those amino acids shown in FIG. 9 (SEQ. ID NO: 2), or may have supplementary amino acids at the N- or C-terminus. For example, tags facilitating purification may be added. The protein may also be fused at the N- or C-terminus to a heterologous protein. A particularly preferred embodiment of the invention is a protein comprising a homodimer of the PSOMT1 sequence of FIG. 9, having an Mr of approximately 85 kDa.

According to a second embodiment of the invention, the PSOMT1 protein may comprise or consist of a fragment of the amino acid sequence illustrated in FIG. 9 (SEQ. ID NO: 2), wherein said fragment has a length of at least 20 amino acids, for example at least 40 amino acids and preferably a length of 150 to 354 amino acids.

By protein "fragment" is meant any segment of the full length sequence of FIG. 9 (SEQ. ID NO: 2) which is shorter than the full length sequence. The fragment may be a C- or N-terminal fragment having for example approximately 20 or 60 or 175 or 250 or amino acids, or may be an internal fragment having 20 to approximately 250 amino acids. Preferably the protein fragments have a length of 200 to 350 amino acids, for example 250 to 320 amino acids, or 275 to 300 amino acids. Particularly preferred are fragments having a length of between 255 and 350 amino acids, such as the FIG. 9 (SEQ. ID NO: 2) sequence having undergone truncation at the C- or N-terminal, or short peptides having a length of 20 to 65 amino acids, for example 35 to 50 amino acids.

The protein fragments of the invention may or may not have (R,S)-reticuline 7-O-methyltransferase activity. Normally, fragments comprising at least 250, or at least 300 consecutive amino acids of the protein shown in FIG. 9 (SEQ. ID NO: 2) are enzymatically active, i.e. have O-methyltransferase activity, particularly (R,S)-reticuline 7-O-methyltransferase activity.

A particularly preferred class of peptides according to the invention are peptides which comprise or consist of a stretch (or "tract") of at least 8, preferably at least 10, and most preferably at least 25 amino acids unique to the (R,S)-reticuline 7-O-methyltransferase (PSOMT1) illustrated in FIG. 9 (SEQ. ID NO: 2). By "unique to PSOMT1" is meant a tract of amino acids which is not present in other plant O-methyltransferases as listed in Table II below. These PSOMT1-specific peptides typically have a length of 10 to 100 amino acids, for example 12 to 70 amino acids, or 18 to 50 amino acids. Such peptides can be used for generation of PSOMT1-specific antibodies for immunodetection and immunopurification techniques.

In general, the PSOMT1 fragments of the invention may consist exclusively of part of the FIG. 9 (SEQ. ID NO: 2) sequence. Alternatively, they may additionally comprise supplementary amino acids which are heterologous to the illustrated *P. somniferum* enzyme, for example N- and/or C-terminal extensions. Such supplementary amino acids may be amino acids from O-methyltransferase enzymes from species other than *P. somniferum*, thus providing a chimeric (R,S)-reticuline 7-O-methyltransferase enzyme, or may be purification tags, fusion proteins etc.

According to a third preferred embodiment of the invention, the protein comprises or consists of a "variant" of the amino acid sequence of FIG. 9 (SEQ. ID NO: 2). By "variant" is meant a protein having at least 70% identity with the amino acid sequence of FIG. 9 (SEQ. ID NO: 2) over a length of at least 300 amino acids, and preferably at least 80%, 85% or 90% identity with the amino acid sequence of FIG. 9, over a length of at least 300 amino acids. Particularly preferred are variants having at least 90% or at least 95% identity, for example 95.5 to 99.9% identity. Preferred variants have sequences which differ from the amino acid sequence illustrated in FIG. 9 (SEQ. ID NO: 2) by insertion, replacement and/or deletion of at least one amino acid, for example insertion, replacement and/or deletion of one to 10 amino acids, or one to five amino acids. Variants differing from the FIG. 9 (SEQ. ID NO: 2) sequence by one to ten amino acid replacements are particularly preferred, for example two, three, four or five amino acid substitutions. Such variants may or may not have (R,S)-reticuline 7-O-methyltransferase activity, as defined previously. Preferably, the variants have this activity.

Particularly preferred "variant" proteins of the invention are allelic variants of PSOMT1, or PSOMT1 proteins arising from expression of other members of a PSOMT1 gene family. For example, there may exist within a given species of *Papaver*, or within a given genotype of *P. somniferum*, variants of the PSOMT1 gene containing a number of single point polymorphisms, some of which may give rise to changes in amino acid sequence. Typically, these variants contain one to fifteen amino acid substitutions, for example one to ten, or one to six, with respect to the FIG. 9 (SEQ. ID NO: 2) sequence. Amino acid changes are usually conservative, with a neutral amino acid such as isoleucine or serine being replaced by another neutral amino acid such as valine or alanine, or an acidic amino acid such as aspartic acid being replaced by another acidic amino acid such as glutamic acid etc. (R,S)-reticuline 7-O-methyltransferase activity is usually conserved.

Other PSOMT1 variants of the invention include proteins which again have at least 70% identity with the amino acid sequence of FIG. 9 (SEQ. ID NO: 2) over a length of at least 300 amino acids, and which contain at least part of one or more of the conserved amino acid motifs shown as shaded boxes (Motifs A, J, K, B, C and L) in FIG. 3 (PSOMT1 sequence). In accordance with this variant of the invention, the partial motifs which are conserved are as follows:

| | | |
|---|---|---|
| Part of Motif A: | LVDVGGG | (SEQ ID NO:26) |
| Part of Motif B: | PXXDAXXMK | (SEQ ID NO:27) |
| Part of Motif C: | XGKVI | (SEQ ID NO:28) |
| Part of Motif J: | DLPHV | (SEQ ID NO:29) |
| Part of Motif K: | HVGGDMF | (SEQ ID NO:30) |
| Part of Motif L: | GKERT | (SEQ ID NO:31) | using the one-letter amino acid code, and wherein "X" represents any amino acid.

The invention thus also includes variants of the FIG. 9 (SEQ. ID NO: 2) protein having the required degree of identity with the FIG. 9 protein (at least 70%) and including for example the LVDVGGGTG (SEQ. ID NO: 32) motif and the AGKERTEAE (SEQ ID NO: 33) motif.

The PSOMT1 proteins of the invention can be used for the production of methylated catechols or methylated tetrahydrobenzylisoquinolines. An example of such a method comprises the steps of:

i) contacting in vitro a PSOMT2 protein having (R,S)-reticuline 7-O-methyltransferase activity with a substrate chosen from guaiacol, isovanillic acid, (R)-reticuline, (S)-reticuline, (R,S)-orientaline, (R)-protosinomenine and (R,S)-isoorientaline at a pH between 7.5 to 9, ii) recovering the methylated catechols or methylated tetrahydrobenzylisoquinolines thus produced.

The PSOMT1 proteins used in this in vitro method are generally used in purified, dimeric form.

In addition to the proteins described above, the invention also relates to nucleic acid molecules encoding the PSOMT1 proteins, for example cDNA, single and double stranded DNA and RNA, genomic DNA, synthetic DNA, or to their complementary sequences.

Examples of particularly preferred nucleic acid molecules are molecules comprising or consisting of:

i) the nucleic acid sequence illustrated in FIG. 8 (SEQ. ID NO: 1, or ii) a fragment of the nucleic acid sequence illustrated in FIG. 8 (SEQ ID NO: 1), said fragment having a length of at least 60 nucleotides, or iii) a variant of the sequence illustrated in FIG. 8 (SEQ ID NO: 1), said variant having at least 70% identity with the sequence of FIG. 8 (SEQ ID NO: 1) over a length of at least 900 bases, or iv) a sequence complementary to sequences (i), (ii) or (iii), or v) any one of sequences (i), (ii) or (iii) in double-stranded form, or vi) the RNA equivalent of any of sequences (i), (ii), (iii), (iv) or (v).

The sequence of FIG. 8 (SEQ. ID NO: 1) indicates the coding region of the full length cDNA of *P. somniferum* (R,S)-reticuline 7-O-methyltransferase. The invention encompasses any nucleic acid molecule which consists of this coding sequence, or which additionally includes further nucleotides at either the 5' and/or 3' extremities, for example, the full sequence shown in FIG. 8 (SEQ ID NO: 1), which includes 5' and 3' untranslated regions. The additional nucleotides may be other untranslated regions, or endogenous or exogenous regulatory sequences, or fusions to other coding regions.

Also within the scope of the invention are molecules comprising or consisting of fragments of the nucleic acid sequence illustrated in FIG. 8 (SEQ. ID NO: 1), said fragments having a length of at least 25 nucleotides, preferably 30 nucleotides, and most preferably at least 60 nucleotides In the context of the invention, a nucleic acid "fragment" signifies any segment of the full length sequence of FIG. 10 (SEQ. ID NO: 15) which is shorter than the full length sequence. Preferred fragments of the invention have a length of 60 to 1430 nucleotides, and encode an enzymatically active (R,S)-reticuline 7-O-methyltransferase.

Other fragments include 5'- or 3'-terminal truncations, or an internal fragment, of the sequence of FIG. 8, for example a fragment of approximately 75 to 1400 nucleotides. Preferred fragments have a length of 80 to 1300 nucleotides, for example 90 to 1200 or 100 to 1000 nucleotides. Shorter fragments having a length of 18 or 30 to 150 nucleotides can be used as primers in nucleic acid amplification reactions, enabling the isolation of related O-methyltransferases of species other than *P. somniferum*, or of different lines within a given species of *Papaver*. When the nucleic acid fragment of the invention is relatively short, i.e. between approximately 18 to 50 nucleotides, it usually comprises a stretch (or tract) of at least 18 nucleotides which is unique to the (R,S)-reticuline 7-O-methyltransferase. Such unique tracts may for example encode protein fragments which do not occur in other plant O-methyltransferases as shown in Table II, or may be chosen from the untranslated regions shown in FIG. 8. These fragments, or their complementary sequences, are useful in amplification reactions.

Molecules comprising fragments of the FIG. 8 (SEQ. ID NO: 1) sequence also include genomic DNA which may contain at least one intron, and which can thus be considered to be an assembly of fragments linked by one or more intronic sequences. Such a genomic molecule may further comprise the endogenous (R,S)-reticuline 7-O-methyltransferase regulatory sequences.

The nucleic acid molecules of the invention may also be a variant of the nucleotide sequence illustrated in FIG. 8 (SEQ. ID NO: 1), wherein said variant has at least 70% identity with the sequence of FIG. 8 (SEQ. ID NO: 1) over a length of at least 900 bases, and preferably at least 80%, or at least 90% or at least 95% identity with the sequence of FIG. 8 (SEQ. ID NO: 1), over a length of at least 900 bases. Particularly preferred variants show 95 to 99.9% identity for example 96 to 99.5% identity. Most preferred variants differ from the sequence of FIG. 8 (SEQ. ID NO: 1) by insertion, replacement and/or deletion of at least one nucleotide, for example replacement of one to two hundred nucleotides, or insertion of a total of 2 or more nucleotides, for example an insertion of 3 to 100 nucleotides, whilst conserving at least 70% identity with the FIG. 8 (SEQ. ID NO: 1) sequence. An example of a sequence variant is a sequence that is degenerate with respect to the sequence illustrated in FIG. 8 (SEQ. ID NO: 1).

Typically, nucleic acid variants of the invention have the capacity to hybridise to the sequence illustrated in FIG. 8 (SEQ. ID NO: 1) in stringent conditions, partcularly to the coding sequence illustrated in FIG. 8. Stringent conditions are for example those set out in Sambrook et al., Molecular Cloning: A Laboratory Manual, Cold Spring Harbor Laboratories, Cold Spring Harbor, N.Y., USA, 1989 pages 387-389, paragraph 11.

Particularly preferred nucleic acid variants of the invention are variants of the (R,S)-reticuline 7-O-methyltransferase gene occurring within a given species of *P. somniferum*, such as allelic variants or gene family members. Allelic variants usually have up to 1% difference in nucleotide sequence with respect to the full length coding sequence, for example with respect to the coding sequence shown in FIG. 8, and usually share the same chromosomal location. Such allelic variants thus show at least 99% identity with the coding sequence shown in FIG. 8 (SEQ. ID NO:1), for example at least 99.3 or at least 99.7% identity, and comprise at least one nucleic acid substitution with respect to this sequence, for example 2 to 10 base changes. The changes are usually single base changes and may be silent or may give rise to amino acid differences.

According to the invention, members of a gene family usually differ by up to 5% with respect to the full length coding sequence, for example with respect to the coding sequence shown in FIG. 8, and need not share the same chromosomal location. Such family members thus show at least 95% identity with the coding sequence shown in FIG. 8 (SEQ. ID NO: 1), for example at least 97% identity, and comprise at least one nucleic acid substitution with respect to this sequence, for example 2 to 50 base changes, more particularly 2 to 30 changes. Again, the changes are usually single base changes and may be silent or may give rise to amino acid differences.

Further variants of the nucleic acid sequences of the invention include mutants obtained for example, by mutagenesis, either directed or random, producing new enzymes with modified specificities. For example, mutants capable of methylating a broader range of substrates, or capable of methylating substrates totally different from the natural substrates can be generated, for example mutants capable of methylating morphine to produce codeine. Variants generated in such directed evolution methods generally differ by up to 5% with respect to the full length coding sequence, for example with respect to the coding sequence shown in FIG. 8 (SEQ. ID NO: 1), showing at least 95% identity with the coding sequence shown in FIG. 8, for example at least 97% identity, and comprise at least one nucleic acid substitution, insertion or deletion with respect to this sequence, for example 2 to 50 base changes, more particularly 2 to 15 changes. The changes are usually give rise to amino acid differences.

More particularly, the invention concerns the so-called PSOMT2 proteins illustrated in FIG. 3 (SEQ. ID NO: 3), and FIG. 13 (SEQ. ID NO: 21), and variants and derivatives thereof. These PSOMT2 proteins are allelic variants of the *P. somniferum* (R,S)-norcoclaurine 6-O-methyltransferase.

According to a preferred embodiment, the invention thus concerns a protein having O-methyltransferase activity, particularly (R,S)-norcoclaurine 6-O-methyltransferase activity, said protein comprising or consisting of:
i) the PSOMT2 amino acid sequence illustrated in FIG. 3 (SEQ. ID NO: 3) or,
ii) the PSOMT2a amino acid sequence illustrated in FIG. 13 (SEQ. ID NO: 21) or
iii) a fragment of the PSOMT2 or PSMOT2a amino acid sequences illustrated in FIG." 3 (SEQ. ID NO: 3), and FIG. 13 (SEQ. ID NO: 21), said fragment having at least 100 amino acids, or
iv) a variant of the PSOMT2 or PSMOT2a amino acid sequence of FIG. 3(SEQ. ID NO: 3), or FIG. 13 (SEQ. ID NO: 21), said variant having at least 70% identity, and preferably at least 80% or 90% identity, most preferable at least 97% identity, for example at least 99% identity, with the PSOMT2 amino acid sequence of FIG. 3 (SEQ. ID NO: 3) or FIG. 13 (SEQ. ID NO: 21), over a length of at least 300 amino acids.

The fragments or variants of the PSOMT2 and PSOMT2a protein as defined above will be collectively referred to herein as the "PSOMT2 derivatives".

Again, as with the PSOMT1 proteins, the PSOMT2 protein and derivatives are preferably in dimeric form, i.e. the protein is a dimer comprising two protein sub-units, each sub-unit being chosen from any one of proteins (i), (ii), (iii) or (iv) as defined above. Both homodimers and heterodimers of the PSOMT2 proteins and derivatives are within the scope of the invention. In the context of the invention, the designation "PSOMT2 proteins" includes dimeric forms of said proteins. The proteins may be purified from natural sources, or made by chemical or recombinant techniques.

According to a preferred embodiment of the invention, the protein comprises or consists of a variant of the amino acid sequence illustrated in FIG. 14 (SEQ. ID NO: 23). Such a variant has from 1 to 10 amino acid substitutions, deletions and/or insertions with respect to the amino acid sequence illustrated in FIG. 14 (SEQ. ID NO: 23), and has not more than 99.8% identity with the full length sequence of FIG. 14. The said variant has O-methyltransferase activity, particularly (R,S)-norcoclaurine 6-O-methyltransferase activity.

The invention thus encompasses allelic variants of the FIG. 14 (SEQ. ID NO: 23) sequence, which preferably have between 97% and 99.7% identity with the full length sequence of FIG. 14, for example between 98.5% and 99.5% identity. Such variants include those having from 1 to 5 amino acid substitutions with respect to the FIG. 14 sequence, particularly 2 to four amino acid substitutions.

It has been established by the inventors that the naturally occurring variants of the *P. somniferum* (R,S)-norcoclaurine 6-O-methyltransferase are particularly susceptible to have variation at any one of amino acid positions 93, 150, 233, 245 and 274, wherein the amino acid positions referred to are those illustrated in FIGS. 14 (SEQ. ID NO: 23) and 16 (SEQ. ID NO: 25). Consequently, the invention includes PSOMT2 proteins wherein at least one amino acid substitution, deletions or insertion occurs at a position chosen from positions 93, 150, 233, 245 and 274, as illustrated in FIG. 14. Preferably, the variation is a single amino acid substitution, occurring at one or more of positions 93, 150, 233, 245 and 274, for example at positions 93, 235 and 245.

Typically, the PSMOT2 proteins of the invention comprise or consist of the sequence illustrated in FIG. 16 (SEQ ID NO: 25), wherein "X" at positions 93, 150, 233, 245 and 274 represents the occurrence of any amino acid, but are preferably chosen from the following amino acids:

```
X93:        Pro, Val;
X150:       Val, Glu;
X233:       Ser, Pro;
X245:       Ala, Gly;
X274:       Gly, Val,
```

Advantageously, X93 is not Pro when X150, X233, X245, X274 together represent the following amino acids: Xaa150 is Glu, Xaa233 is Ser, Xaa245 is Ala and Xaa274 is Gly.

According to one embodiment of this mode of the invention, the methyl transferase enzyme thus comprises the full length PSOMT2 (R,S)-norcoclaurine 6-O-methyltransferase protein whose amino acid sequence is shown in FIG. 3 (PSOMT2) (SEQ. ID NO: 3 and SEQ. ID NO: 19), or the full length PSOMT2a (R,S)-norcoclaurine 6-O-methyltransferase protein whose amino acid sequence is shown in FIG. 13 (PSOMT2)(SEQ. ID NO: 21). These proteins have 346 amino acids, and a molecular weight of approximately 43 kDa (Genebank accession number AY268894). According to this embodiment of the invention, the full length PSOMT2 enzymes may be obtained by isolation and purification to homogeneity from cell suspension culture, or from plant parts of *P. somniferum*, at any stage of development, and from latex of mature or immature plants. Alternatively, the enzyme may be produced by recombinant means in suitable host cells such as plant cells or insect cells. The protein may consist exclusively of those amino acids shown in FIG. 3 or 13, or may have supplementary amino acids at the N- or C-terminus. For example, tags facilitating purification may be added. The protein may also be fused at the N- or C-terminus to a heterologous protein. A particularly preferred embodiment of the invention is a protein comprising a homodimer of the PSOMT2 sequence of FIG. 3 or 13, having an Mr of approximately 85 kDa.

The PSOMT2 proteins and derivatives as defined above, and dimers thereof, generally have O-methyltransferase activity, particularly (R,S)-norcoclaurine 6-O-methyltransferase activity. In the context of the invention, "(R,S)-norcoclaurine 6-O-methyltransferase activity" signifies the capacity of a protein to carry out methylation of (R,S)-norcoclaurine, (S)-norcoclaurine, and/or (R)-norcoclaurine at the 6-hydroxyl group, forming (R,S)-coclaurine, forming (S)-coclaurine, and (R)-coclaurine, respectively. The proteins of the invention catalyse this reaction both in vivo and in vitro. The 6-O-methylation by PSOMT2 and derivatives preferably occurs over a wide range of pH (pH 6.0 to 9.0), and a temperature optimum of 37 to 41° C. The (R,S)-norcoclaurine 6-O-methyltransferase activity in vitro is measured using the experimental protocols described in the Examples below on purified enzyme as obtained from a eukaryotic cell, for example further to heterologous expression in a eukaryotic host, or any other suitable technique.

The PSOMT2 proteins and derivatives of the invention also have the in vitro capacity to methylate substrates other than (R,S)-norcoclaurine, (S)-norcoclaurine, and/or (R)-norcoclaurine. In particular, the PSOMT2 proteins have the capacity to methylate in vitro the following substrates, in addition to (R)-reticuline, (S)-reticuline, at the 6-hydroxy position: (R)-norprotosinomenine, (S)-norprotosinomenine and (R,S)-isoorientaline. Optimal pH for these 6-O-methylations is at pH 7.5, ith a temperature optima again at 37 to 41° C.

In accordance with another embodiment of the PSOMT2 aspect of the invention, the protein or peptide may be comprise or consist a portion or fragment of the full length protein illustrated in FIG. 16. Such a fragment generally has a length of 25 to 345 amino acids, for example 100 to 340 amino acids, or 150 to 300 amino acids, and spans that part of the protein which encompasses at least one of positions 93, 150, 233, 245 and 274, wherein X has the previously ascribed meaning.

By PSOMT2 protein "fragment" is meant any segment of the full length sequence of FIG. 16 which is shorter than the full length sequence. The fragment may be a C- or N-terminal fragment having for example approximately 25 or 60 or 175 or 250 or amino acids, or may be an internal fragment having 30 to approximately 250 amino acids. Preferably the PSOMT2 protein fragments have a length of 200 to 350 amino acids, for example 250 to 320 amino acids, or 275 to 300 amino acids. Particularly preferred are fragments having a length of between 255 and 350 amino acids, such as the FIG. 3 or FIG. 13 sequence having undergone truncation at the C- or N-terminal.

Examples of PSOMT2 protein fragments and peptides thus include proteins comprising or consisting of amino acids 1 to 150 of the FIG. 3 or FIG. 13 sequence, or amino acids 139 to 250, or 230 to 346 of the FIG. 3 or FIG. 13 sequence.

The PSOMT2 protein fragments of the invention may or may not have (R,S)-norcoclaurine 6-O-methyltransferase activity. Normally, fragments comprising at least 250, or at least 300 consecutive amino acids of the protein shown in FIG. 9 (SEQ. ID NO: 2) are enzymatically active, i.e. have O-methyltransferase activity, particularly (R,S)-norcoclaurine 6-O-methyltransferase activity.

A particularly preferred class of PSOMT2 peptides according to the invention are peptides which comprise or consist of a stretch (or "tract") of at least 8, preferably at least 10, and most preferably at least 25 amino acids unique to the (R,S)-norcoclaurine 6-O-methyltransferase (PSOMT2) illustrated in FIGS. 3 (SEQ. ID NO: 3) or 13 (SEQ. ID NO: 21). By "unique to PSOMT2" is meant a tract of amino acids which is not present in other plant O-methyltransferases as listed in Table II below. These PSOMT2-specific peptides typically have a length of 10 to 100 amino acids, for example 12 to 70 amino acids, or 18 to 50 amino acids. Such peptides can be used for generation of PSOMT2-specific antibodies for immunodetection and immunopurification techniques.

Other PSOMT2 variants of the invention include proteins which again have at least 95 or 97% identity with the amino acid sequence of FIG. 3 (SEQ. ID NO: 3) or FIG. 13 (SEQ. ID NO: 21) over a length of at least 300 amino acids, and which contain at least part of one or more of the conserved amino acid motifs shown as shaded boxes (Motifs A, J, K, B, C and L) in FIG. 3 (PSOMT2 sequence). In accordance with this variant of the invention, the partial motifs which are conserved are as follows:

```
Part of Motif A:    LVDVGGG     (SEQ ID NO:26)
Part of Motif B:    PXXDAXXMK   (SEQ ID NO:27)
Part of Motif C:    XGKVI       (SEQ ID NO:28)
Part of Motif J:    DLPHV       (SEQ ID NO:29)
Part of Motif K:    HVGGDMF     (SEQ ID NO:30)
Part of Motif L:    GKERT       (SEQ ID NO:31)
``` using the one-letter amino acid code, and wherein "X" represents any amino acid.

The PSOMT2 proteins of the invention can be used for the production of methylated tetrahydrobenzylisoquinolines. An example of such a method comprises the steps of:
i) contacting in vitro a protein having norcoclaurine 6-O-methyltransferase activity, for example a PSOMT2 protein or derivative as defined above, with a substrate chosen from (R,S)-norcoclaurine, (R,S)-isoorientaline, (R)-norprotosinomenine and (S)-norprotosinomenine at pH 6.0 to 9.0,
ii) recovering the methylated tetrahydrobenzylisoquinolines thus produced.

The PSOMT2 proteins used in this in vitro method are generally used in purified, dimeric form.

In addition to the PSOMT2 proteins described above, the invention also relates to nucleic acid molecules encoding the PSOMT2 proteins, for example cDNA, single and double stranded DNA and RNA, genomic DNA, synthetic DNA, or to their complementary sequences.

Examples of particularly preferred nucleic acid molecules are molecules comprising or consisting of:
i) the nucleic acid sequence illustrated in FIG. 10 (SEQ. ID NO: 18), or
ii) the nucleic acid sequence illustrated in FIG. 11 (SEQ. ID NO: 20), or
iii) a fragment of the nucleic acid sequence illustrated in FIG. 10 or 11, said fragment having a length of at least 60 nucleotides, or
iv) a variant of the sequence illustrated in FIG. 10 or 11, said variant having at least 70% identity, for example at least 80% or 90% identity, and preferably at least 99 to 99.9% identity, with the sequence of FIG. 10 or 11 over a length of at least 900 bases, or
v) a sequence complementary to sequences (i), (ii), (iii), or (iv),
vi) any one of sequences (i), (ii), (iii), (iv) or (v) in double-stranded form, or
vii) the RNA equivalent of any of sequences (i), (ii), (iii), (iv), (v) or (vi).

Preferred nucleic acid molecule of the invention are variants of the sequence illustrated in FIG. 12 (SEQ. ID NO: 22). Such variants comprise or consist of a sequence having from 1 to 10 nucleotide insertions, substitutions or deletions with respect to the nucleic acid sequence illustrated in FIG. 12, and have not more than 99.9% identity, preferably not more than 99.5% identity with the full length sequence of FIG. 12. These variants include the different norcoclaurine 6-O-methyltransferase gene alleles, and preferably differ from the FIG. 12 sequence by 1 to 5 single nucleotide substitutions, which may or may not give rise to amino acids changes.

Such variants include the nucleic acid molecule comprising or consisting of the PSOMT2 coding sequence illustrated in FIG. 10, or the PSOMT2a coding sequence illustrated in FIG. 11. The invention encompasses any nucleic acid molecule which consists of either one of the coding sequences illustrated in FIGS. 10 and 11, or which additionally includes further nucleotides at either the 5' and/or 3' extremities, for example, the full sequence shown in FIG. 10 (SEQ. ID NO: 18), which includes 5' and 3' untranslated regions. The additional nucleotides may be other untranslated regions, or endogenous or exogenous regulatory sequences, or fusions to other coding regions.

Also within the scope of the invention are molecules comprising or consisting of fragments of the nucleic acid sequence illustrated in FIG. 10 or 11. Such fragments having a length of at least 25 nucleotides, preferably 30 nucleotides, and most preferably at least 60 nucleotides In the context of the invention, a PSOMT2 nucleic acid "fragment" signifies any segment of the full length sequence of FIG. 10 or 11 which is shorter than the full length sequence. Preferred fragments of the invention have a length of 60 to 1040 nucleotides, and encode an enzymatically active norcoclaurine 6-O-methyltransferase.

Particularly preferred PSOMT2 nucleic acid fragments comprise or consist of a stretch (or tract) of the sequence illustrated in FIG. 10 (SEQ. ID NO: 18) or FIG. 11(SEQ. ID NO: 20), said fragment having from 60 to 1000 nucleotides, and spans that part of the molecule which encodes at least one of amino acids 93, 150, 233, 245 and 274. Typical fragment lengths are from 100 to 500 bases.

Other PSOMT2 fragments include 5'- or 3'-terminal truncations, or an internal fragment, of the sequence of FIG. 10 or 11, for example a fragment of approximately 75 to 1400 nucleotides. Preferred fragments have a length of 80 to 1300 nucleotides, for example 90 to 1200 or 100 to 1000 nucleotides. Shorter fragments having a length of 15 or 18 to 150 nucleotides can be used as primers in nucleic acid amplification reactions, enabling the isolation of related O-methyltransferases of species other than *P. somniferum*, or of different lines within a given species of *Papaver*. Examples of such sequences are molecules having a length of 15 to 300 nucleotides, for example 20 to 50 nucleotides; and comprising at least 15 consecutive nucleotides of the 5' sequence from nucleotide 1 to nucleotide 31 of the sequence illustrated in FIG. 10 (SEQ. ID NO: 18). A further example is a molecule having a length of 15 to 300 nucleotides, for example 20 to 50 nucleotides, and comprising at least 15 consecutive nucleotides of the 3' extremity of the sequence illustrated in FIG. 10 (SEQ. ID NO: 18), extending from nucleotide 1210 to nucleotide 1320.

When the nucleic acid fragment of the invention is relatively short, i.e. between approximately 18 to 50 nucleotides, it usually comprises a stretch (or tract) of at least 18 nucleotides which is unique to the PSOMT2 gene. Such unique tracts may for example encode protein fragments which do not occur in other plant O-methyltransferases as shown in Table II, or may be chosen from the untranslated regions shown in FIG. 10. These fragments, or their complementary sequences, are useful in amplification reactions.

Molecules comprising fragments of the FIG. 10 or FIG. 11 sequence also include genomic DNA which may contain at least one intron, and which can thus be considered to be an assembly of fragments linked by one or more intronic sequences. Such a genomic molecule may further comprise the endogenous norcoclaurine 6-O-methyltransferase regulatory sequences.

Typically, nucleic acid variants of the invention have the capacity to hybridise to the sequence illustrated in FIG. 10 or 11 in stringent conditions, particularly to the coding sequence illustrated in FIG. 10 or 11. Stringent conditions are for example those set out in Sambrook et al., Molecular Cloning: A Laboratory Manual, Cold Spring Harbor Laboratories, Cold Spring Harbor, N.Y., USA, 1989 pages 387-389, paragraph 11.

Nucleic acid variants and fragments of the invention may encode an enzymatically active protein or not. Preferred variants encode proteins having O-methyltransferase activity, particularly norcoclaurine 6-O-methyltransferase activity, as defined previously.

Further variants of the PSOMT2 nucleic acid sequences of the invention include mutants obtained for example, by mutagenesis, either directed or random, producing new enzymes with modified specificities. For example, mutants capable of methylating a broader range of substrates, or capable of methylating substrates totally different from the natural substrates can be generated, for example mutants capable of methylating morphine to produce codeine. Variants generated in such directed evolution methods generally differ by up to 5%, for example by up to 2 or 3% with respect to the full length coding sequence, for example with respect to the coding sequence shown in FIG. 10 or 11, showing at least 95% identity with the coding sequence shown in FIG. 10 or 11, for example at least 97% identity, and comprise at least one nucleic acid substitution, insertion or deletion with respect to this sequence, for example 2 to 50 base changes, more particularly 2 to 15 changes. The changes usually give rise to amino acid differences.

In a more general context, the invention also encompasses nucleic acid molecules that are complementary to any of the foregoing molecules, variants and fragments, both PSOMT1 and PSOMT2 derivatives. In the context of the invention, "complementary" means that Watson-Crick base-pairs can form between a majority of bases in the complementary sequence and the reference sequence. Preferably, the complementarity is 100%, but one or two mismatches in a stretch of twenty or thirty bases can be tolerated. Additionally, complementary stretches may be separated by non-complementary stretches.

The nucleic acid molecules of the invention may contain at least one nucleotide analogue in replacement of, or in addition to, a naturally occurring nucleotide. Ribonucleotide and deoxyribonucleotide derivatives or modifications are well known in the art, and are described, for example, in Principles of Nucleic Acid Structure (Ed, Wolfram Sanger, Springer-Verlag, New York, 1984), particularly pages 159-200), and in the CRC Handbook of Biochemistry (Second edition, Ed, H. Sober, 1970). A large number of modified bases are found in nature, and a wide range of modified bases have been synthetically produced. For example, amino groups and ring nitrogens may be alkylated, such as alkylation of ring nitrogen atoms or carbon atoms such as N1 and N7 of guanine and C5 of cytosine; substitution of keto by thioketo groups; saturation of carbon=carbon double bonds. Bases may be substituted with various groups, such as halogen, hydroxy, amine, alkyl, azido, nitro, phenyl and the like. Examples of suitable nucleotide analogues are listed in Table I below. In accordance with this embodiment of the invention, synthetic genes comprising one or more nucleotide analogues, for example methylated bases, are made, for example by chemical synthesis, and can be introduced into cells for a transient expression process in vivo.

TABLE I

Nucleotide Analogues

| Abbreviation | Description |
|---|---|
| ac4c | 4-acetylcytidine |
| chm5u | 5-(carboxyhydroxylmethyl)uridine |
| cm | 2'-O-methylcytidine |
| cmnm5s2u | 5-carboxymethylaminomethyl thiouridine |
| d | dihydrouridine |
| fm | 2'-O-methylpseudouridine |
| galq | β,D-galactosylqueosine |
| gm | 2'-O-methylguanosine |
| I | inosine |
| i6a | N6-isopentenyladenosine |
| m1a | 1-methyladenosine |
| m1f | 1-methylpseudouridine |
| m1g | 1-methy[guanosine |
| m1l | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5u | 5-methylaminomethyluridine |
| mam5s2u | 5-methoxyaminomethyl-2-thiouridine |
| manq | β,D-mannosylmethyluridine |
| mcm5s2u | 5-methoxycarbonylmethyluridine |
| mo5u | 5-methoxyuridine |
| ms2i6a | 2-methylthio-N6-isopentenyladenosine |
| ms2t6a | N-((9-β-ribofuranosyl-2-methylthiopurine-6-yl)carbamoyl)threonine |
| mt6a | N-((9-β-ribofuranosylpurine-6-yl)N-methylcarbamoyl)threonine |
| mv | uridine-5-oxyacetic acid methylester |
| o5u | uridine-5-oxyacetic acid (v) |
| osyw | wybutoxosine |
| p | pseudouridine |
| q | queosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-β-D-ribofuranosylpurine-6-yl)carbamoyl)threoninetm 2'-O-methyl-5-methyluridine |
| um | 2'-O-methyluridine |
| yw | wybutosine |
| x | 3-(3-amino-3-carboxypropyl)uridine, (acp3)u |

TABLE I-continued

Nucleotide Analogues

| Abbreviation | Description |
|---|---|
| araU | β,D-arabinosyl |
| araT | β,D-arabinosyl |

The nucleic acid molecules of the invention can be used to transform or transfect eukaryotic and prokaryotic cells. To this end, the sequences are usually operably linked to transcription regulatory sequences such as promoters, transcription terminators, enhancers etc. The operable link between the (R,S)-reticuline 7-O-methyltransferase-derived coding sequence or the norcoclaurine 6-O-methyltransferase coding sequence, and the regulatory sequence(s) may be direct or indirect, i.e. with or without intervening sequences. They may also contain internal ribosome entry sites (IRES). The regulatory sequences may be endogenous to the coding sequence, i.e. they are the regulatory sequences naturally associated with the (R,S)-reticuline 7-O-methyltransferase gene or the norcoclaurine 6-O-methyltransferase gene in the genome of the plant. Alternatively, the regulatory sequences may be heterologous to the (R,S)-reticuline 7-O-methyltransferase sequence or the norcoclaurine 6-O-methyltransferase sequence. In this latter case the resulting construct forms a chimeric gene, comprising a coding sequence derived from the methyltransferase gene, operably linked to at least one heterologous transcription regulatory sequence. In the context of the invention, the term "coding sequence" signifies a DNA sequence that encodes a functional RNA molecule. The RNA molecule may be untranslated, or may encode an enzymatically-active protein, or enzymatically-inactive protein.

The invention also relates to eukaryotic and prokaryotic cells transformed or transfected by the nucleic acid sequences derived from the (R,S)-reticuline 7-O-methyltransferase gene, and from the norcoclaurine 6-O-methyltransferase gene. An example of a suitable prokaryotic cell is a bacterial cell. Examples of suitable eukaryotic cells are yeast cells, vertebrate cells such as mammalian cells, for example mouse, monkey, or human cells, or invertebrate cells such as insect cells. Plant cells are particularly preferred. In the context of the present invention, the term "plant" is to be understood as including mosses and liverworts. The plant cells can be any type of plant cells, including monocotyledonous or dicotyledonous plant cells. The cells may be differentiated cells or callus for example suspension cultures. Cells of the genus *Papaver* are particularly preferred.

According to the invention, cells are transfected or transformed using techniques conventional in the art, in conditions allowing expression of the (R,S)-reticuline 7-O-methyltransferase gene or derivatives, or norcoclaurine 6-O-methyltransferase or derivatives. A number of transformation techniques have been reported for *Papaver*. For example, microprojectile bombardment of cell suspension cultures may be used. Transformation may also be effected using *Agrobacterium tumefaciens*, or *Agrobacterium rhizogenes*, using either cell suspension cultures or tissue explants. A number of further techniques are available and are known to the skilled man.

When transforming cells with the methyltransferase genes or derivatives of the invention, the choice of cell is made depending upon the objective to be achieved.

One objective is to produce recombinant (R,S)-reticuline 7-O-methyltransferase enzyme, or derivatives thereof. A preferred method for producing proteins having this activity comprises:
  i) transforming or transfecting a cell with a (R,S)-reticuline 7-O-methyltransferase gene or derivatives as defined above, in conditions permitting the expression of the protein having (R,S)-reticuline 7-O-methyltransferase activity,
  ii) propagating the said cells, and
  iii) recovering the thus-produced protein having (R,S)-reticuline 7-O-methyltransferase activity.

A further objective is to produce recombinant norcoclaurine 6-O-methyltransferase enzyme, or derivatives thereof. A preferred method comprises the steps of:
  i) transforming or transfecting cells with a (R,S)-norcoclaurine 6-O-methyltransferase gene or derivatives thereof, as defined above, in conditions permitting the expression of the protein having norcoclaurine 6-O-methyltransferase activity,
  ii) propagating the said cells, and
  iii) recovering the thus-produced protein having norcoclaurine 6-O-methyltransferase activity.

For the purpose of producing recombinant enzyme, any of the above listed cell-types can be used. Plant cells such as cells of a *Papaver* species, or insect cells, as demonstrated in the examples below, are particularly suitable. Bacterial cells, such as *E. coli*, can also be used.

The enzymes of the invention, and their derivatives and variants, can also be used in semi-synthetic drug preparation, where necessary in association with other enzymes involved in alkaloid biosynthesis, for example in the preparation of the analgesics codeine and morphine, and the antitussive noscapine, the vasodilator papaverine and the antimicrobial benzo[c]phenanthridine sanguinarine.

The (R,S)-reticuline 7-O-methyltransferase genes and derivatives of the invention can also be used for producing 7-O-methylreticuline. Such a method comprises the steps of:
  i) introducing a nucleic acid molecule encoding a protein of the invention having (R,S)-reticuline 7-O-methyltransferase activity into a plant cell which is capable of expressing (R)-reticuline or (S)-reticuline,
  ii) propagating said plant cell in conditions wherein the (R,S)-reticuline 7-O-methyltransferase and the (R)-reticuline or (S)-reticuline are expressed, thereby producing a multiplicity of cells,
  iii) recovering 7-O-methylreticuline from said multiplicity of cells.

Likewise, the (R,S)-norcoclaurine 6-O-methyltransferase genes and derivatives of the invention can also be used for producing (R) or (S)-coclaurine. Such a method comprises the steps of:
  i) introducing an exogenous nucleic acid molecule encoding a protein having norcoclaurine 6-O-methyltransferase activity into a plant cell which is capable of expressing (S)-norcoclaurine,
  ii) propagating said plant cell in conditions wherein the norcoclaurine 6-O-methyltransferase activity and the (S)-norcoclaurine are expressed, thereby producing a multiplicity of cells,
  iii) recovering (S)-coclaurine from said multiplicity of cells.

In such methods the multiplicity of cells is preferably a cell culture of differentiated or undifferentiated cells.

Various aspects of the invention are illustrated in the Figures:

FIG. 1. Schematic biosynthetic pathway leading from (S)-norcoclaurine to (S)-scoulerine, (R)-reticuline and laudanine in *P. somniferum*. The pathway from (S)-norcoclaurine to (S)-reticuline is central to the isoquinoline alkaloids accumulated in opium poppy. (S)-Reticuline is a branch point intermediate that is subsequently oxidized at C-1-N to lead into the morphinan pathway, or at N—CH$_3$ to proceed on to (S)-scoulerine-derived alkaloids such as the benzo[c]phenanthridines. In addition, reticuline can be 7-O-methylated to laudanine.

Figure 2:
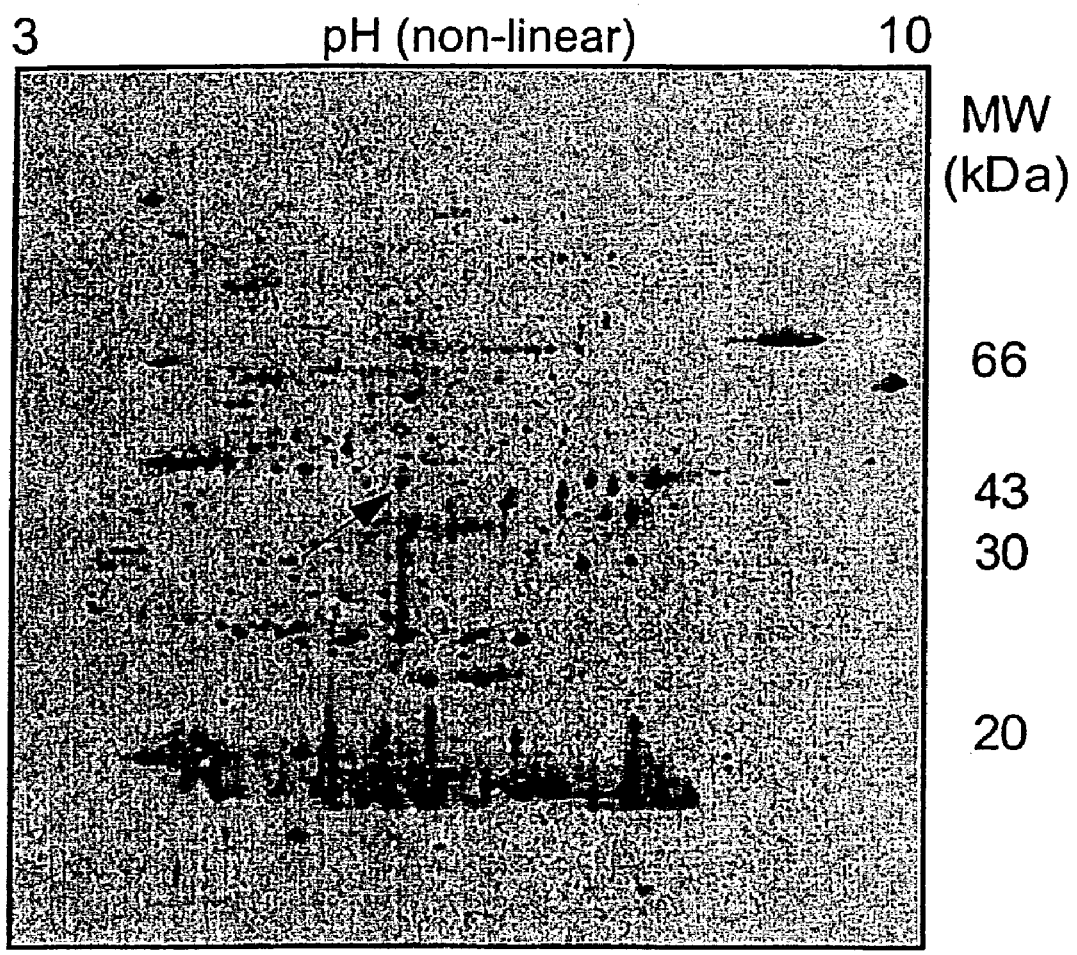

FIG. 2. Two-dimensional gel electrophoretic pattern of the cytosolic fraction proteins of latex collected from *P. somniferum* capsules. Fifty micrograms protein were loaded per gel and were visualized by silver staining. The arrow points to the position of the O-methyltransferase described in this work. Protein spots from Coomassie Brilliant Blue R-250-stained gels were excised, the proteins digested in situ with endoproteinase Lys-C and the peptides resolved and sequenced according to (24).

FIG. 3. Amino acid sequence comparison of PSOMT1 (SEQ ID NO:2) and PSOMT2 (SEQ ID NO:3) from *P. somniferum*. The shaded motifs are conserved regions motif A, J, K, B, C and L indicative of plant methyltransferases according to Joshi and Chiang (2). These sequence signatures were based upon plant methyltransferase amino acid sequence comparisons and were not functionally defined. They are mainly used to indicate whether unidentified proteins may be O-methyltransferases.

Figure 4:
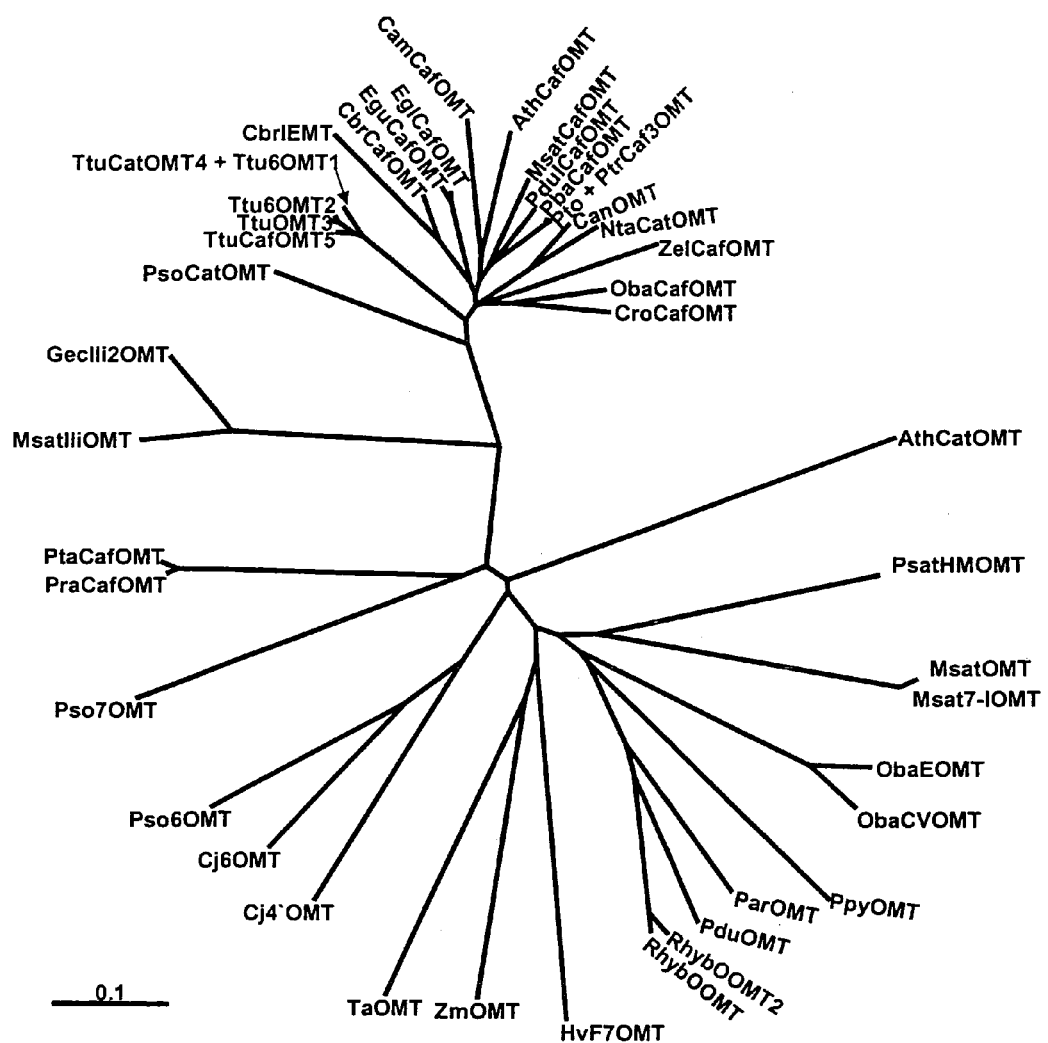

FIG. 4. Phylogenetic tree of plant methyltransferases of defined and of unknown function. Forty-four amino acid sequences of proteins of plant origin were compared to generate a tree that indicates the phylogenetic relationship between PSOMT1, PSOMT2 and other putative and defined O-methyltransferases. PSOMT1 grouped most closely to two putative methyltransferases from pine, while PSOMT2 was most similar to (R,S)-norcoclaurine 6-O-methyltransferase of (S)-reticuline biosynthesis from *C. japonica* (5). Two additional (R,S)-norcoclaurine 6-O-methyltransferases from *T. tuberosum* are clearly more related to caffeic acid O-methyltransferases from a variety of plant species than to either PSOMT1 or PSOMT2. The abbreviations and accession numbers of the amino acid sequences referred to in FIG. 4 are shown in Table II:

TABLE II

| Abbreviation | Plant | Enzyme | Database accession |
|---|---|---|---|
| CbrIEMT | *Clarkia breweri* | (Iso)eugenol O-methyltransferase | AAC01533 |
| CbrCafOMT | *Clarkia breweri* | caffeic acid O-methyltransferase | AAB71141 |
| TtuCatOMT4 | *Thalictrum tuberosum* | caffeic acid O-methyltransferase | AAD29845 |
| Ttu6OMT1 | *Thalictrum tuberosum* | caffeic acid O-methyltransferase | AAD29841 |
| Ttu6OMT2 | *Thalictrum tuberosum* | caffeic acid O-methyltransferase | AAD29842 |
| TtuOMT3 | *Thalictrum tuberosum* | caffeic acid/catechol O-methyltransferase | AAD29843 |
| TtuCafOMT5 | *Thalictrum tuberosum* | caffeic acid O-methyltransferase | AAD29845 |
| PsoCatOMT | *Papaver somniferum* | catechol O-methyltransferas | AY268895 |
| GecIli2OMT | *Glycyrrhiza echinata* | Isoliquiritigenin 2'OMT | BAA13683 |
| MsatIIiOMT | *Medicago sativa* | isoliquiritigenin 2'-O-methyltransferase | AAB48059 |
| PtaCafOMT | *Pinus taeda* | caffeic acid O-methyltransferase | AAC49708 |
| PraCafOMT | *Pinus radiata* | caffeic acid O-methyltransferase | AAD24001 |
| Pso7OMT | *Papaver somniferum* | reticuline 7-O methyltransferase | AY268893 |
| Pso6OMT | *Papaver somniferum* | norcoclaurine 6-O methyltransferase | AY268894 |
| Cj6OMT | *Coptis japonica* | norcoclaurine 6-O methyltransferase | BAB08004 |
| Cj4'OMT | *Coptis japonica* | 3'hydroxy-N-methylcoclaurine 4'O-methyltransferase | BAB08005 |
| TaOMT | *Triticum aestivum* | o-methyltransferase | AAD10485 |
| ZmOMT | *Zea mays* | O-methyltransferase | P47917 |
| HvF7OMT | *Hordeum vulgare* | | S52015 |
| RhybOOMT | *Rosa hybrida* | orcinol O-methyltransferase | AAM23004 |
| RhybOOMT2 | *Rosa hybrida* | orcinol O-methyltransferase | AAM23005 |
| PduOMT | *Prunus dulcis* | O-methyltransferase | CAA11131 |
| ParOMT | *Prunus armeniaca* | O-methyltransferase | AAB71213 |
| PpyOMT | *Pyrus pyrifolia* | O-methyltransferase | BAA86059 |
| ObaCVOMT | *Ocimun basilicum* | chavicol O-methyltransferase1 | AF435007 |
| ObaEOMT | *Ocimun basilicum* | eugenol O-methyltransferase1 | AF435008 |
| Msat7-IOMT | *Medicago sativa* | isoflavone-7-O-methyltransferase | T09254 |
| MsatOMT | *Medicago sativa* | o-methyltransferase iomt2003 | T09299 |
| PsatHMOMT | *Pisum sativum* | 6a-hydroxymaackiain methyltransferase | T06786 |
| AthCatOMT | *Arabidopsis thaliana* | catechol O-methyltransferas1 | T04963 |
| CrocafOMT | *Catharanthus roseus* | caffeic acid O-methyltransferase | AAK20170 |
| ObaCafOMT | *Ocimun basilicum* | caffeic acid O-methyltransferase1 | AAD38189 |
| ZelCafOMT | *Zinnia elegans* | caffeic acid O-methyltransferase | AAA86718 |
| NtaCafOMT | *Nicotiana tabacum* | catechol O-methyltransferase | S36403 |
| CanOMT | *Capsicum annuum* | O-diphenol-O-methyltransferase | T12259 |
| PtoCafOMT | *Populus tomentosa* | caffeic acid 3-O-methyltransferase | AAF63200 |
| PtrCaf3OMT | *Populus tremuloides* | caffeic acid 3-O-methyltransferase | Q00763 |
| PbaCafOMT | *Populus balsamifera* | caffeic acid O-methyltransferase | CAA01820 |
| PdulCafOMT | *Prunus dulcis* | caffeic acid O-methyltransferase | CAA58218 |
| MsatCafOMT | *Medicago sativa* | caffeic acid O-methyltransferase | AAB46623 |
| AthCafOMT | *Arabidopsis thaliana* | caffeic acid O-methyltransferase1 | AAB96879 |
| CamCafOMT | *Chrysosplenium americanum* | caffeic acid O-methyltransferase1 | AAA86982 |
| EglCafOMT | *Eucalyptus globulus* | caffeic acid O-methyltransferase1 | AAD50440 |
| EguOMT | *Eucalyptus gunnii* | caffeic acid O-methyltransferase1 | CAA52814 |

Figure 5:
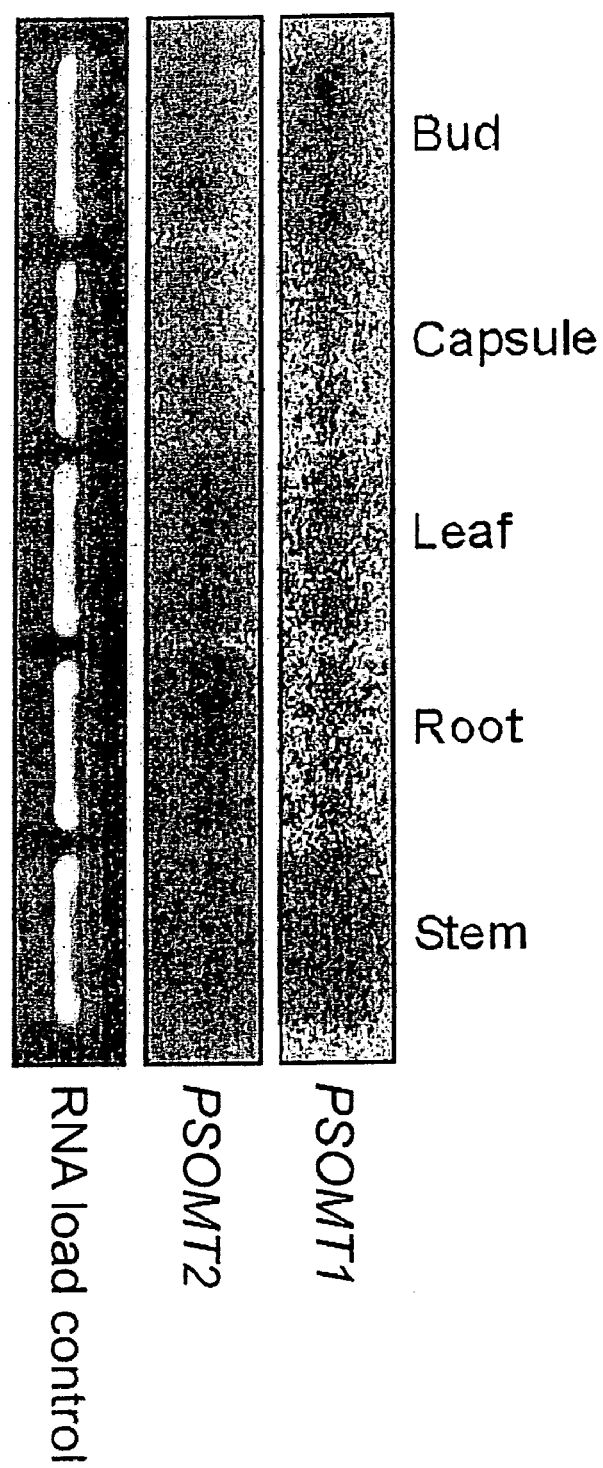

FIG. 5. RNA gel blot analysis of PSOMT1 and PSOMT2. Top panel, PSOMT1 is expressed predominantly in bud and stem, and to a much lesser degree, in leaf of *P. somniferum*. Middle panel, PSOMT2 is expressed in bud, stem, leaf and root, and to a lesser degree in capsule. These results were obtained after blotting a *P. somniferum* RNA gel and hybridizing to $^{32}$P-labeled full-length PSOMT1 or PSOMT2. Radioactivity was visualized by phosphorimagery. The bottom panel is a photograph of ethidium bromide-visualized RNA in the gel prior to blotting. This served as an RNA loading control.

FIG. 6. Chemical structures of the substrates methylated by either PSOMT1 or PSOMT2.

Figure 7:
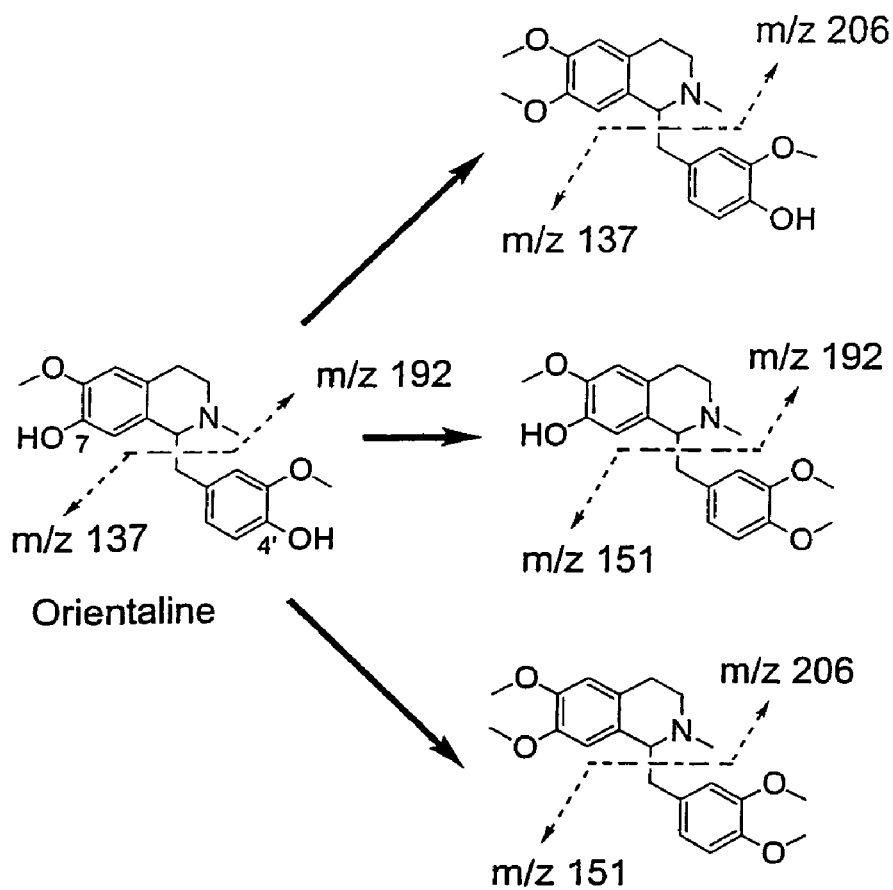

FIG. 7. Mass spectrometric fragmentation of orientaline transformed by PSOMT1. Each substrate and the corresponding enzymic reaction products were analyzed by HPLC-MS. Orientaline is shown as an example here due to the complex methylation patterns that resulted after incubation with PSOMT1 in the presence of AdoMet. Three products can be identified, resulting from monomethylation at the isoquinoline moiety, monomethylation at the benzyl moiety and double methylation. The main product is monomethylated at the free isoquinoline hydroxyl at C-7.

FIG. 8. Nucleotide sequence of cDNA encoding (R,S)-reticuline 7-O-methyltransferase from *P. somniferum* (PSOMT1; SEQ ID NO:1). The cDNA encoding PSOMT1 contains 1437 bp including a 5' non-coding region of 40 bp, a 3' non-coding region of 329 bp and a complete open reading frame of 1068 bp encoding 355 amino acids. Location of the first and last nucleotide of the coding sequence indicated in bold type.

FIG. 9. Amino acid sequence of (R,S)-reticuline 7-O-methyltransferase from *P. somniferum* (PSOMT1; SEQ ID NO:2).

FIG. 10. Nucleotide sequence of cDNA encoding (R,S)-norcoclaurine 6-O-methyltransferase from *P. somniferum* (PSOMT2; SEQ ID NO:18). The cDNA encoding PSOMT2 contains 1346 bp including a 5' non-coding region of 59 bp, a 3' non-coding region of 246 bp and a complete open reading frame of 1041 bp encoding 346 amino acids. Location of the first and last nucleotide of the coding sequence indicated in bold type, "n" represents any nucleotide A, C, T or G, preferably T.

FIG. 11. Nucleotide sequence of cDNA encoding (R,S)-norcoclaurine 6-O-methyltransferase from *P. somniferum* (variant PSOMT2a; SEQ ID NO:20), encompassing the reading frame only. This sequence was generated by PCR with primers at the start and stop codons. Nucleotides in bold type and singly underlined are those that differ from the PSOMT2 sequence as illustrated in FIG. 10, and which give rise to amino acid changes. The nucleotide in bold type and doubly underlined is the nucleotide which differs from the PSOMT2 sequence as illustrated in FIG. 10 and which does not lead to an amino acid change.

FIG. 12. Nucleotide sequence of cDNA encoding putative (R,S)-norcoclaurine 6-O-methyltransferase from *P. somniferum* (according to Facchini et al., GenBank accession AY217335; SEQ ID NO:22): the coding sequence is from nucleotides 28 to 1068, as numbered in FIG. 12.

FIG. 13. Amino acid sequence of (R,S)-norcoclaurine 6-O-methyltransferase from *P. somniferum* (variant PSOMT2a; SEQ ID NO:21). In bold, underlined, are variable amino acids.

FIG. 14. Amino acid sequence of putative (R,S)-norcoclaurine 6-O-methyltransferase from *P. somniferum* (according to Facchini et al., GenBank accession AY217335; SEQ ID NO:23).

FIG. 15. Alignment of amino acid sequences of variants of the (R,S)-norcoclaurine 6-O-methyltransferase from *P. somniferum*: Abbreviations: "AO" signifies the PSOMT2 sequence of the invention, as illustrated in FIG. 3 (SEQ ID NO:3); "SH" signifies the PSOMT2a variant of the invention, as illustrated in FIG. 13, (SEQ ID NO:21), and "PF" signifies the putative (R,S)-norcoclaurine 6-O-methyltransferase according to Facchini et al (GenBank AY217335; SEQ ID NO:23).

FIG. 16: Amino acid sequence of (R,S)-norcoclaurine 6-O-methyltransferase from *P. somniferum* (SEQ ID NO:25), wherein X represents positions at which amino acid variation occurs, and may be any amino acid.

EXAMPLES

The abbreviations used in the following Examples are: AdoMet, S-adenosyl-L-methionine; COMT, catechol O-methyltransferase; RT-PCR, reverse transcriptase-polymerase chain reaction; HPLC, high performance liquid chromatography; RACE, rapid amplification of DNA ends; MS, mass spectrometry; bp, base pairs; OMT, O-methyltransferase; PSOMT, *Papaver somniferum* O-methyltransferase.

A. Experimental Procedures

Plant Material—*P. somniferum* seedlings were routinely grown aseptically on Gamborg B5 medium (15) containing 0.8% agar in a growth chamber at 22° C., 60% relative humidity under cycles of 16 h light/8 h dark with a light intensity of 85 µmol sec$^{-1}$ m$^{-2}$ per µA. Differentiated *P. somniferum* plants were grown either outdoors in Saxony-Anhalt or in a greenhouse at 24° C., 18 h light and 50% humidity.

Generation of Partial cDNAs from *P. somniferum*—Partial cDNAs encoding O-methyltransferases from *P. somniferum* were produced by PCR using cDNA generated by reverse transcription of mRNA isolated from floral stem. DNA amplification using either Taq or Pfu polymerase was performed under the following conditions: 3 min at 94° C., 35 cycles of 94° C., 30 s; 50° C., 30 s; 72° C., 1 min. At the end of 35 cycles, the reaction mixtures were incubated for an additional 7 min at 72° C. prior to cooling to 4° C. The amplified DNA was resolved by agarose gel electrophoresis, the bands of approximately correct size (400 bp) were isolated and subcloned into pGEM-T Easy (Promega) prior to nucleotide sequence determination. The specific sequences of the oligodeoxynucleotide primers used are given in the Results section.

Generation of Full-Length cDNAs—The sequence information requisite to the generation of a full-length cDNA was derived from the nucleotide sequence of the partial cDNA produced as described in the Results section. The complete nucleotide sequence was generated in two steps using one O-methyltransferase-specific PCR primer (PSOMT1: 5'-AGT CAT TTC CAT CTG GTC GCA ACA-3' (SEQ. ID NO: 4) for 5'-RACE and 5'-ATG GAT ACT GCA GAA GAA AGG TTG-3' (SEQ. ID NO:5) for 3'-RACE; PSOMT2: 5'-ATA AGG GTA AGC CTC AAT TAC AGA TTG-3' (SEQ. ID NO: 6) for 5'-RACE and 5'-GCT GCA GTG AAA GCC ATA ATC T-3' (SEQ. ID NO: 7) for 3'-RACE) and one RACE-specific primer as specified by the manufacturer. The 5'- and 3'-RACE-PCR experiments were carried out using a SMART cDNA amplification kit (Clontech). RACE-PCR was performed using the following PCR cycle: 3 min at 94° C., 25 cycles of 94° C., 30 s; 68° C., 30 s; 72° C., 3 min. At the end of 25 cycles, the reaction mixtures were incubated for an additional 7 min at 72° C. prior to cooling to 4° C. The amplified DNA was resolved by agarose gel electrophoresis, the bands of the expected size (PSOMT1: 990 bp for 5'-RACE and 1177 bp for 3'-RACE; PSOMT2: 1124 bp for 5'-RACE and 671 bp for 3'-RACE) were isolated and subcloned into pGEM-T Easy prior to sequencing.

The full-length clone was generated in one piece using the primers PSOMT1: 5'-TAT CGG ATC CAT GGA TAC TGC AGA A-3' (SEQ. ID NO: 8) and 5'-TTA GGC GGC CGC TTA TTC TGG AAA GGC-3' (SEQ. ID NO: 9) or PSOMT2: 5'-TAT CGG ATC CAT GGA AAC AGT AAG C-3' (SEQ. ID NO:10) and 5'-TTA GGC GGC CGC TTA ATA AGG GTA AGC-3' (SEQ. ID NO: 11) for PCR with P. somniferum floral stem cDNA as template. The final primers used for cDNA amplification contained recognition sites for the restriction endonucleases BamHI and NotI, appropriate for subcloning into pFastBac Hta (Life Technologies) for functional expression. DNA amplification was performed under the following conditions: 3 min at 94° C., 35 cycles of 94° C., 30 s; 60° C., 30 s; 72° C., 2 min. At the end of 35 cycles, the reaction mixtures were incubated for an additional 7 min at 72° C. prior to cooling to 4° C. The amplified DNA was resolved by agarose gel electrophoresis, the band of approximately correct size (PSOMT1: 1068 bp; PSOMT2: 1041 bp) was isolated and subcloned into pCR4-TOPO (Invitrogen) prior to nucleotide sequence determination.

Heterologous Expression and Enzyme Purification—The full-length cDNA generated by RT-PCR was ligated into pFastBac HTa that had been digested with restriction endonucleases BamHI and NotI. The recombinant plasmid was transposed into baculovirus DNA in the *Escherichia coli* strain DH10BAC (Life Technologies) and then transfected into *Spodoptera frugiperda* Sf9 cells according to the manufacturer's instructions. The insect cells were propagated and the recombinant virus was amplified according to (16,17). INSECT-XPRESS serum-free medium (Bio Whittaker) was used in the enzyme expression experiments.

After infection of 20 ml suspension grown insect cells had proceded for 3-4 days at 28° C. and 130 rpm, the cells were removed by centrifugation under sterile conditions at 900× g for 5 min at 4° C. All subsequent steps were performed at 4° C. The pellet was discarded and to the medium was added 0.73 g NaCl, 2.5 ml glycerol and 50 µl □-mercaptoethanol. The pH was adjusted to 7.0 with 1.0 M NaOH. The His-tagged O-methyltransferase was then purified by affinity chromatography using a cobalt resin (Talon, Clontech) according to the manufacturer's instructions.

Enzyme assay and product identification: The O-methylation reactions catalysed by the two O-methyltransferases were assayed at least two times in duplicate according to Rüffer et al. (1983a; 1983b) as follows. Substrate (25 nmol), [methyl-3H]-AdoMet (20,000 dpm, 0.4 fmol), AdoMet (10 nmol) Tris/HCl buffer pH 8.0 (10 µmol), ascorbate (5 µmol) and 5-10 µg of enzyme were incubated in a total volume of 150 µl at 35° C. for 5-60 min. The enzymic reaction was terminated by addition of 200 µl ethylacetate. The organic phase (300 µl) was added to 3 ml high flash point liquid scintillation cocktail (Packard) and the radioactivity quantified with a Beckman LS6000TA liquid scintillation counter. For Km determinations, substrate concentration was varied from 0 to 400 µm.

The identity of the enzymic reaction products was ascertained by HPLC-MS using a Finnigan MAT TSQ 7000 (electrospray voltage 4.5 kV, capillary temperature 220° C., carrier gas $N_2$) coupled to a Micro-tech Ultra-Plus Micro-LC equipped with an Ultrasep RP18 column; 5 µm; 1×10 mm), Solvent system (A) 99.8% (v/v) $H_2O$, 0.2% HOAc (B) 99.8% $CH_3CN$ (v/v), 0.2% HOAc; gradient: 0-15 min 10-90% B, 15-25 min 90% B; flow 70 µl $min^{-1}$). The collision-induced dissociation (CID; collision energy, -25 eV; collision gas, argon; collision pressure, $1.8×10^{-3}$ Torr) mass spectra for the tetrahydrobenzylisoquinoline alkaloids were recorded.

General Methods—Total RNA was isolated and RNA gels were run and blotted as described previously (20). Genomic DNA was isolated and DNA gels were run and blotted according to (21). cDNA clones were labeled by PCR labeling with [□-$^{32}$P]dATP. Hybridized RNA on RNA gel blots and DNA on DNA gel blots were visualized with a STORM phosphor imager (Molecular Dynamics). The entire nucleotide sequence on both DNA strands of the full-length clone was determined by dideoxy cycle sequencing using internal DNA sequences for the design of deoxyoligonucleotides as sequencing primers. Saturation curves and double reciprocal plots were constructed with the Fig. P program Version 2.7 (Biosoft, Cambridge, UK). The influence of pH on enzyme activity was monitored in sodium citrate (pH 4-6), sodium phosphate (pH 6-7.0) and Tris-HCl (pH 7.0-9), glycine/NaOH (pH 9-10.5) buffered solutions.

B. Results

Amino Acid Sequence Analysis of a Putative O-Methyltransferase and Isolation of the Corresponding cDNA—Latex was harvested from field-grown P. somniferum by incising capsules 3-6 days after flower petal fall. The exuded latex was immediately added to ice-cold potassium phosphate buffer containing 20 mM sodium ascorbate and 500 mM mannitol, pH 7.2. The latex buffer ratio was approximately 1:1. Particulates were removed by centrifugation (22,23) prior to two-dimensional polyacrylamide gel electrophoretic resolution of the proteins in the 1000× g supernatant according to (24) (FIG. 2). Internal amino acid microsequencing of proteins in the size range expected for plant methyltransferase monomers (approximately 40 kDa) yielded five peptides from a single protein that was homologous to O-methyltransferases. The amino acid sequences of these five peptides are as follows:

| | | |
|---|---|---|
| OMT-Pep 1 | RTEAE | (SEQ ID NO:24) |
| OMT-Pep 2 | VIIVDCVLRPDGNDL | (SEQ ID NO:12) |
| OMT-Pep 3 | VGGDMFVDIPEADAV | (SEQ ID NO:13) |
| OMT-Pep 4 | ILLNNAGFPRYNVIRTPAFPcIIEA | (SEQ ID NO:14) |
| OMT-Pep 5 | DGFSGIAGSLVDGG | (SEQ ID NO:15) |

Degenerated oligodeoxynucleotide primers were derived from OMT-Pep 1 and OMT-Pep 5 as shown below:

OMT-Pep 5 sense primer:         (SEQ ID NO:16)
5'-GCI GGI A/T C/G I C/T TI GTI GAC/T GTI GGI GG-3'

OMT-Pep 1 antisense primer:      (SEQ ID NO:17)
5'-C/T TC IGC C/T TC IGT ICG/T C/T TC CTT-3'

PCR amplification of P. somniferum cDNA prepared from stem poly $(A)^+$ RNA yielded a DNA band of the expected size (approximately 400 bp) upon analysis by agarose gel electrophoresis. Subcloning of the PCR product into pGEM-T Easy followed by nucleotide sequence determination of randomly chosen samples identified two independent O-methyltransferase-encoding partial cDNA clones denoted PSOMT1 and PSOMT2. Each O-methyltransferase partial sequence was used to design specific oligodeoxynucleotide primers for RACE-PCR, by which cDNAs containing the entire open reading frames for both O-methyltransferases were generated. The details of these experiments are provided in the Experimental Procedures section.

Sequence Analyses of O-Methyltransferases—Translation of the complete nucleotide sequences of PSOMT1 and PSOMT2 yielded polypeptides of 356 and 347 amino acids, respectively. Amino acid sequence alignment carried out using the program from Heidelberg Unix Sequence Analysis Resources demonstrated 38.9% identity of the two proteins. Amino acid sequences of O-methyl transfer enzymes contain consensus sequences putatively involved in catalysis. Conserved motifs A, B, C, J, K and L proposed by Joshi and Chiang (2) are shown for PSOMT1 and PSOMT2 as shaded regions in FIG. 3.

A phylogenetic diagram of forty-four putative and defined O-methyltransferase amino acid sequences from seventeen plants was constructed using the Phylogeny Inference Package program (PHYLIP Version 3.57c) (FIG. 4). Among these forty-four sequences, PSOMT1 showed the closest relationship to a catechol 3-O-methyltransferase from *Pinus taeda* (loblolly pine) (32) and to a putative caffeic acid O-methyltransferase from Monterey pine *Pinus radiata*. In contrast, PSOMT2 grouped together with norcoclaurine 6-O-methyltransferase from *C. japonica* (5). The next most closely related sequence was 3'-hydroxy-N-methylcoclaurine 4'-O-methyltransferase, also from *C. japonica* (5). These new *P. somniferum* O-methyl transfer enzymes group more closely to isoquinoline biosynthetic O-methyltransferases from *C. japonica* than to those identified from *T. tuberosum* (4). Table III below shows results of some of the sequence comparisons, indicating % amino acid identity. Abbreviations are given in Table II above. The results of the phylogenetic analysis formed the basis for the enzymes assays that were later carried out with heterologously expressed cDNAs as reported below.

encodes the cytochrome P-450-dependent monooxygenase (S)-N-methylcoclaurine 3'-hydroxylase (8,9) common to the biosynthetic pathways of all the *P. somniferum* alkaloids, salAT that encodes salutaridinol 7-O-acetyltransferase (13) and cor1 that encodes codeinone reductase (14), both specific to morphine biosynthesis, are all expressed in bud, capsule, leaf, root and stem. This gene transcript distribution of PSOMT2 taken together with the results of the phylogenetic analysis is congruent with PSOMT2 encoding norcoclaurine 6-O-methyltransferase of (S)-reticuline biosynthesis (4,5).

The comparative transcript distribution and phylogenetic analysis of PSOMT1 suggests that the gene product may be involved in tetrahydrobenzylisoquinoline alkaloid formation, but not directly in either the (S)-reticuline or the morphine biosynthetic pathways.

Purification and Functional Characterization of Recombinant Enzymes—The PSOMT1 and PSOMT2 cDNAs were each constructed to express the recombinant proteins with six histidine residues elongating the amino terminus. The proteins were then purified from *S. frugiperda* Sf9 cell culture medium in one step by cobalt affinity chromatography to yield electrophoretically homogeneous proteins. PSOMT1 and PSOMT2 each have relative molecular masses of 43 kDa as determined by SDS-PAGE. This compares with the calculated molecular masses of 39,841 and 38,510 based on the translation of the nucleotide sequences. The native relative molecular masses were determined by gel filtration on a calibrated Sephacryl 200 column (Pharmacia). PSOMT1 and PSOMT2 are each homodimers with an Mr of 85 and 80 kDa, respectively. This is consistent with that observed for norcoclaurine 6-O-methyltransferases of (S)-reticuline biosynthesis in *T. tuberosum* (4).

Radioassay of pure, recombinant O-methyltransferases using [methyl-$^3$H]-AdoMet together with each of forty different substrates demonstrated that PSOMT1 and PSOMT2 are relatively substrate-specific (Table IV below). PSOMT1 methylates the simple catechols guaiacol and isovanillic acid as well as the tetrahydrobenzylisoquinolines (R)-reticuline, (S)-reticuline, (R,S)-orientaline, (R)-protosinomenine and (R,S)-isoorientaline. PSOMT2 is more specific, methylating only (R,S)-norcoclaurine, (R)-norprotosinomenine, (S)-norprotosinomenine and (R,S)-isoorientaline. The limited quan-

TABLE III

Amino Acid Sequence comparisons

| | Ps6OMT | Ps7OMT | ttu6OMT1 | ttu6OMT2 | Cj6OMT | Cj 4OMT | PraCafOMT | PtaOMT |
|---|---|---|---|---|---|---|---|---|
| Ps6OMT | — | 36 | 29.1 | 28 | 63.4 | 52.2 | | |
| Ps7OMT | 36 | — | 32.3 | 32 | 35.7 | 32.3 | 44.1 | 44.4 |
| ttu6OMT1 | 29.1 | 32.3 | — | 93.6 | 30.8 | 30.6 | | |
| ttu6OMT2 | 28 | 32 | 93.6 | — | 30 | 32 | | |
| Cj6OMT | 63.4 | 35.7 | 30.8 | 30 | — | 50.4 | | |
| Cj 4OMT | 52.2 | 32.3 | 30.6 | 32 | 50.4 | — | | |

Gene Expression Analyses—RNA gel blot analysis suggests that PSOMT1 is expressed predominantly in bud and stem, and to a much lesser degree, in leaf of *P. somniferum* (FIG. 5). In contrast, PSOMT2 transcript is detectable in bud, stem, leaf and root, and to a lesser degree in capsule (FIG. 5). The distribution of PSOMT2 transcript parallels the distribution of transcript of several other genes of tetrahydrobenzylisoquinoline biosynthesis in *P. somniferum*. Cyp80b1 that tities of (R,S)-orientaline prohibited further kinetic characterization of methylation of this particular substrate.

PSOMT1 has a pH optimum at 8.0 for guaiacol, (R)-reticuline and (S)-reticuline. The optimal pH for methylation of (R)-protosinomenine and isovanillic acid are 9.0 and 7.5, respectively, whereas the optimal pH for methylation of (R,S)-isoorientaline ranges from 7.5-9.0. PSOMT2 methylates (R,S)-norcoclaurine over a wide pH range (6.0-9.0). Methyl transfer to (R)-norprotosinomenine, (S)-norprotosinomenine and (R,S)-isoorientaline has an optimum at pH 7.5. The temperature optima for PSOMT1 with various the substrates are: guaiacol, (R)-reticuline and (S)-reticuline (37° C.), (R)-protosinomenine (39° C.), (R,S)-isoorientaline and isovanillic acid (37-41° C.). PSOMT2 optimally methylated all substrates at 37-41° C.

The kinetic parameters determined for methylation of each substrate of PSOMT1 and PSOMT2 are shown in Table V. As designated by the ratio $k_{cat}/K_m$, PSOMT1 methylates (R)-reticuline and (S)-reticuline with equal efficiency. Both substrates occur in *P. somniferum*, but only (R)-reticuline is specific to morphine biosynthesis. The high $k_{cat}/K_m$, ratio for guaiacol (135% of those values determined for reticuline) does not correlate with in vivo significance, since this simple catechol has not been reported to occur in *P. somniferum*. Likewise, (R)-protosinomenine, (R,S)-isoorientaline and isovanillic acid do not occur in this plant. The highest $k_{cat}/K_m$, ratio for PSOMT2 was obtained with (R,S)-norcoclaurine as substrate. The next best substrates are (R)- and (S)-norprotosinomenine with values equal to 55% of that obtained for norcoclaurine. However, norprotosinomenines do not naturally occur in *P. somniferum*.

TABLE IV

Substrate specificities of PSOMT1 and PSOMT2

| Substrate | PSOMT1 | PSOMT2 |
|---|---|---|
| Phenolics: | | |
| 1 Catechol | 0 | 0 |
| 2 Protocatechuic acid | 0 | 0 |
| 3 Dopamine | 0 | 0 |
| 4 Caffeic acid | 0 | 0 |
| 5 Guaiacol | 242 | 0 |
| 6 Isovanillic acid | 40 | 0 |
| 7 Vanillic acid | 0 | 0 |
| Isoquinoline alkaloids: | | |
| 8 (R,S)-Norcoclaurine | 0 | 100[a] |
| 9 (S)-Coclaurine | 0 | 0 |
| 10 (R,S)-Isococlaurine | 0 | 0 |
| 11 (R,S)-4'-O-methylcoclaurine | 0 | 0 |
| 12 (R,S)-Nororientaline | 0 | 0 |
| 13 (R)-Norprotosinomenine | 0 | 26 |
| 14 (S)-Norprotosinomenine | 0 | 26 |
| 15 (R)-Norreticuline | 0 | 0 |
| 16 (S)-Norreticuline | 0 | 0 |
| 17 (R)-7-Dehydroxy-norreticuline | 0 | 0 |
| 18 (S)-7-Dehydroxy-norreticuline | 0 | 0 |
| 19 (R,S)-N-Methylcoclaurine | 0 | 0 |
| 20 (R,S)-6-O-Methyllaudanosoline | 0 | 0 |
| 21 (S)-4'-O-Methyllaudanosoline | 0 | 0 |
| 22 (R)-Reticuline | 100[a] | 0 |
| 23 (S)-Reticuline | 100[a] | 0 |
| 24 (R,S)-Orientaline | 48 | 0 |
| 25 (R)-Protosinomenine | 52 | 0 |
| 26 (R,S)-Isoorientaline | 46 | 47 |
| 27 (R,S)-Laudanidine | 0 | 0 |
| 28 (R,S)-Codamine | 0 | 0 |
| 29 (S)-Scoulerine | 0 | 0 |
| 30 (S)-Coreximine | 0 | 0 |
| 31 Salutaridine | 0 | 0 |
| 32 Codeine | 0 | 0 |
| 33 Morphine | 0 | 0 |
| Flavonoids: | | |
| 34 Quercetin | 0 | 0 |
| 35 Quercetin-3-methylether | 0 | 0 |
| 36 Quercetin-7-methylether | 0 | 0 |
| 37 Luteolin | 0 | 0 |
| 38 Morin | 0 | 0 |
| 39 Cyanidin | 0 | 0 |
| Coumarin: | | |
| 40 Esculetin | 0 | 0 |

[a]100% Activity of PSOMT1 and PSOMT2 is 1.5 and 2.0 pmoles/sec/mg total protein, respectively. Assay conditions are given in the experimental.

TABLE V

Kinetic parameters of PSOMT1 and PSOMT2 for various substrates and co-substrate (AdoMet)

| Enzyme | Substrate | $K_m$ AdoMet (µM) | $K_m$ Substrate (µM) | $V_{max}$ Substrate (pmol/s) | $k_{cat}$ Substrate (s⁻¹) | $k_{cat}/K_m$ Substrate (s⁻¹ · mM⁻¹) |
|---|---|---|---|---|---|---|
| PSOMT1 | Guaiacol | 310 | 17 | 6 | 0.1 | 5.9 |
| | (S)-Reticuline | 360 | 16 | 4 | 0.07 | 4.5 |
| | (R)-Reticuline | 310 | 17 | 4 | 0.07 | 4.2 |
| | (R)-Protosinomenine | 320 | 16 | 2 | 0.03 | 1.7 |
| | (R,S)-Isoorientaline | 260 | 17 | 1 | 0.02 | 1.4 |
| | Isovanillic acid | 150 | 14 | 1 | 0.02 | 1.2 |
| PSOMT2 | (R,S)-Norcoclaurine | 100 | 10 | 5 | 0.08 | 7.4 |
| | (R)-Norprotosinomenine | 200 | 5 | 1 | 0.02 | 4.1 |
| | (S)-Norprotosinomenine | 260 | 5 | 1 | 0.02 | 4.0 |
| | (R,S)-Isoorientaline | 280 | 29 | 2 | 0.03 | 1.0 |

Assay conditions are given in the experimental.

Structure Elucidation of Enzymic Products—Initial enzyme activity measurements were carried out using a radioassay. Many of the substrates tested contained more than one site of potential methylation. Since the radioassay is only a facile measure of whether methylation had likely occurred, but does not indicate the position of methyl transfer, each positive assay was repeated with unlabeled substrate and the enzymic product was subjected to HPLC-MS analysis. Tetrahydrobenzylisoquinolines readily cleave at low ionization energies into the corresponding isoquinoline- and benzyl ions. This enables identification of methylation at either moiety. The structures of the ten substrates that were methylated by either PSOMT1 or PSOMT2 are shown in FIG. 6. Each alkaloidal substrate was monitored for purity by HLPC-MS and the fragmentation pattern was determined. Enzymic product fragmentation patterns were then compared to those of substrate. All substrates were methylated by either PSOMT1 or PSOMT2 on the isoquinoline moiety. For example, (R)- or (S)-reticuline ([M+H]$^+$ m/z 330) has the major fragment ions m/z 192 (isoquinoline) and m/z 137 (benzyl). The methylation of (R)- or (S)-reticuline by PSOMT1 results in a product of [M+H]$^+$ m/z 344 (methylated (R)- or (S)-reticuline) with fragment ions at m/z 206 (isoquinoline+CH$_2$) and m/z 137 (unmodified benzyl). Likewise, (R,S)-norcoclaurine ([M+H]$^+$ m/z 272) has the major fragment ions m/z 161 (isoquinoline) and m/z 107 (benzyl). The methylation of (R,S)-norcoclaurine by PSOMT2 results in a product of [M+H]$^+$ m/z 286 (methylated (R,S)-norcoclaurine) with fragment ions at m/z 175 (isoquinoline+CH$_2$) and m/z 107 (unmodified benzyl).

Surprising results were obtained when the PSOMT1 methylation products of (R,S)-orientaline and (R,S)-isoorientaline were analyzed by HPLC-MS. The fragment ions obtained for the methylation products of orientaline are shown in FIG. 7. Methylation of the 7-hydroxyl group resulted in the main enzymic product 7-O-methylorientaline. Approximately 1% of the product produced is the double methylated 7,4'-O-dimethylorientaline (laudanosine) and the monomethylated 4'-O-methylorientaline.

The identification of new O-methyltransferases presented herein follows on from a first attempt to use proteome analysis to identify proteins in latex of *P. somniferum* (24, 30). Latex collected from capsules was resolved into a cytosolic and a vesicular fraction by centrifugation and the cytosolic proteins were then resolved by two-dimensional polyacrylamide gel electrophoresis. From internal amino acid sequence determination of these proteins, one with homology to plant O-methyltransferases was identified. Using RT-PCR followed by RACE-PCR, two cDNAs PSOMT1 and PSOMT2 encoding complete open reading frames were isolated.

A sequence comparison of the translations of PSOMT1 and PSOMT2 with those sequences available in the GenBank/EMBL databases revealed that PSOMT1 grouped with proteins from *P. radiata* of unknown function and that PSOMT2 was likely functionally equivalent to (R,S)-norcoclaurine 6-O-methyltransferase from *C. japonica* (5). Using amino acid sequence comparison to predict the in vivo function of plant O-methyltransferases is not trivial due to the broad substrate specificities that can be found for closely related enzymes (4). To overcome the uncertainties associated with phylogenetic comparison, PSOMT1 and PSOMT2 were each introduced into a baculovirus expression vector and the corresponding proteins PSOMT1 and PSOMT2 were produced in *S. frugiperda* Sf9 cell culture. Forty compounds were tested as potential substrates for the two enzymes. Most of these substances were tetrahydrobenzylisoquinoline alkaloids, but simple catechols and a few common phenylpropanoid-derived compounds were also included. PSOMT1 O-methylated guaiacol, isovanillic acid, (R)-reticuline, (S)-reticuline, (R,S)-orientaline, (R)-protosinomenine and (R,S)-isoorientaline. PSOMT2 O-methylated (R,S)-norcoclaurine, (R)-norprotosinomenine, (S)-norprotosinomenine and (R,S)-isoorientaline.

The broad substrate specificities of plant O-methyltransferases can make the assignment of an in vivo role to these enzymes quite challenging. A comparison of the $k_{cat}/K_m$ ratio for the various substrates suggested that the in vivo substrates for PSOMT1 are likely (R)-reticuline and (S)-reticuline. Guaiacol demonstrated the highest $k_{cat}/K_m$ ratio, but this catechol has not been reported to accumulate in *P. somniferum* and could simply represent a fortuitous methylation in vitro. PSOMT2, on the other hand, clearly methylated (R,S)-norcoclaurine most efficiently. The $k_{cat}/K_m$ ratios for (R)-norprotosinomenine and (S)-norprotosinomenine were 55% of that for (R,S)-norcoclaurine, but norprotosinomenine has been reported to occur in the legume *Erythrina lithosperma*, not in *P. somniferum* (25). The O-methylation of norprotosinomenine, therefore, also appears to be a fortuitous in vitro reaction catalyzed by PSOMT2.

Elucidation of the structures of the enzymic products was done by HPLC-MS. Mass spectroscopic analysis of tetrahydrobenzylisoquinoline alkaloids exploits the ready fragmentation of these types of molecules into two halves, an isoquinoline moiety and a benzyl moiety. Methylation of either portion of the molecule can be readily identified. PSOMT2 O-methylated (R,S)-norcoclaurine, (R)-norprotosinomenine, (S)-norprotosinomenine and (R,S)-isoorientaline on the isoquinoline moiety. In the case of (R,S)-norcoclaurine, both C-6 and C-7 are hydroxylated. (R)-norprotosinomenine, (S)-norprotosinomenine and (R,S)-isoorientaline all have a free hydroxyl group at C-6, but C-7 is methoxylated. This indicates that the position of O-methylation of these molecules is at C-6. Based upon the phylogenetic analysis and the structures of the methylated alkaloidal products, it can be concluded that PSOMT2 encodes the tetrahydroisoquinoline biosynthetic enzyme (R,S)-norcoclaurine 6-O-methyltransferase. In *P. somniferum*, this enzyme participates in the early steps of (S)-reticuline biosynthesis, which intermediate leads to numerous alkaloids of the morphinan, benzo[c]phenanthridine, papaverine and phthalideisoquinoline types that are accumulated in this plant. The distribution of PSOMT2 transcript in bud, stem, leaf, root, and capsule is consistent with this role since these are all major sites of accumulation of one or the other of these alkaloid classes (i.e. morphinans in latex and benzo[c]phenanthridines in root).

The methylating capacity of PSOMT1 was more promiscuous than that of PSOMT2. PSOMT1 O-methylation of guaiacol, isovanillic acid, (R)-reticuline, (S)-reticuline, (R,S)-orientaline, (R)-protosinomenine and (R,S)-isoorientaline resulted in a more complicated product profile. HPLC-MS analysis indicated that (R)-reticuline, (S)-reticuline, (R,S)-orientaline, each of which has a C-6 methoxy group and a C-7 hydroxy moiety, were O-methylated at C-7. In contrast, (R)-protosinomenine and (R,S)-isoorientaline each has a free hydroxyl group at C-6 and is methoxylated at C-7. These molecules were O-methylated by PSOMT1 at C-6. The ratio of $k_{cat}/K_m$ for C-7 O-methylation compared to C-6 O-methylation was 3.8:1, suggesting that C-7 O-methylation is preferred. Multiple products were detected when either (R,S)-orientaline or (R,S)-isoorientaline were used as substrate. In addition to methylation of the isoquinoline half of the tetrahydrobenzylisoquinolines, the benzyl moiety was also methylated. (R,S)-orientaline and (R,S)-isoorientaline differ from the other tetrahydrobenzylisoquinoline substrates in that the benzyl ring is 3'-methoxylated and 4'-hydroxylated. Reticuline and the protosinomenines are 4'-methoxylated and 3'-hydroxylated. The free 4'-hydroxy group of (R,S)-orientaline and (R,S)-isoorientaline is methylated by PSOMT1. 4'-O-methylation appears to occur independent of both hydroxyl groups of the isoquinoline nucleus being methylated, since three products can be identified by HPLC-MS, representing monomethylation at the isoquinoline moiety, monomethylation at the benzyl moiety and double methylation. A heterologously expressed O-methyltransferase from *Catharanthus roseus* cell suspension cultures that methylates the flavonol myricetin at both the 3'- and 5'-hydroxyl groups has recently been reported (26). Given free rotation around the bond between the B and C rings, these two hydroxyl moieties can be seen as chemically equivalent, whereas the two hydroxyl groups methylated by PSOMT1 can be viewed as chemically unique.

The main enzymic reaction product formed by PSOMT1 (approximately 99%) results from monomethylation of the isoquinoline group. Based upon these combined kinetic and mass spectroscopic results, it is concluded that PSOMT1 encodes (R,S)-reticuline 7-O-methyltransferase, a new enzyme of tetrahydrobenzylisoquinoline alkaloid biosynthesis in *P. somniferum*. The product of this reaction, 7-O-methylreticuline (laudanine) is a natural product that has been reported to occur in opium (27) and this occurrence has been confirmed for the variety of *P. somniferum* used herein (A. J. Fist, personal communication). The distribution of PSOMT1 transcript predominantly in bud and stem correlates with latex as the site of laudanine accumulation.

Enzymic O-methylation of tetrahydrobenzylisoquinolines has been reported to be catalyzed by catechol O-methyltrasferase (COMT) isolated from rat liver as part of a program investigating the nature and biosynthetic origin of mammalian alkaloids (28). In that particular report, COMT O-methylated norcoclaurine at the 6-hydroxy- and 7-hydroxy positions in a ratio of 8:2. This low specificity compares to that of norcoclaurine 6-O-methyltransferase characterized from *T. tuberosum*, which methylated tetrahydrobenzylisoquinolines that contained a catechol- and, to a lesser degree, a guaiacol moiety (4). The *P. somniferum* 7-O- and 6-O-methyltransferases characterized herein appear to methylate with higher regiospecificity.

REFERENCES

1. Ibrahim, R. K., Bruneau, A., and Bantignies, B. (1998) *Plant Mol. Biol.* 36, 1-10
2. Joshi, C. P., and Chiang, V. L. (1998) *Plant Mol. Biol.* 37, 663-674
3. Schröder, G., Wehinger, E., and Schröder, J. (2002) *Phytochemistry* 59, 1-8
4. Frick, S., and Kutchan, T. M. (1999) *Plant J.* 17, 329-339
5. Morishige, T., Tsujita, T., Yamada, Y., and Sato, F. (2000) *J. Biol. Chem.* 275, 23398-23405
6. Maury, S., Geoffroy, P., and Legrand, M. (1999) *Plant Physiol.* 121, 215-223
7. Kutchan, T. M. (1998) in *The Alkaloids Vol.* 50, (ed. G. Cordell) Academic Press, San Diego, 257-316
8. Pauli, H. H., and Kutchan, T. M. (1998) *Plant J.* 13, 793-801
9. Huang, F.-C., and Kutchan, T. M. (2000) *Phytochemistry* 53, 555-564
10. Rosco, A., Pauli, H. H., Priesner, W., and Kutchan, T. M. (1997) *Arch. Biochem. Biophys.* 348, 369-377
11. Dittrich, H. and Kutchan, T. M. (1991) *Proc. Natl. Acad. Sci. USA* 88, 9969-9973
12. Facchini, P. J., Penzes, C., Johnson A. G., and Bull, D. (1996) *Plant Physiol.* 112, 1669-1677
13. Grothe, T., Lenz, R., and Kutchan, T. M. (2001) *J. Biol. Chem.* 276, 30717-30723
14. Unterlinner, B., Lenz, R., and Kutchan, T. M. (1999) *Plant J.* 18, 465-475
15. Gamborg, O. L., Miller, R. A., and Ojina, K. (1968) *Exp. Cell. Res.* 50, 151-158
16. Kutchan, T. M., Bock, A., and Dittrich, H. (1994) *Phytochemistry* 35, 353-360
17. Pauli, H., and Kutchan, T. M. (1998) *Plant J.* 13, 793-801
18. Rüffer, M., Nagakura, N., and Zenk, M. H. (1983) *Planta Med.* 49, 131-137
19. Rüffer, M., Nagakura, N., and Zenk, M. H. (1983) *Planta Med.* 49, 196-198
20. Pauli, H., and Kutchan, T. M. (1998) *Plant J.* 13, 793-801
21. Bracher, D., and Kutchan, T. M. (1992) *Arch. Biochem. Biophys.* 294, 717-723
22. Roberts, M. F., McCarthy, D., Kutchan, T. M., and Coscia, C. J. (1983) *Arch. Biochem. Biophys.* 222, 599-609
23. Antoun, M. D., and Roberts, M. F. (1975) *Phytochemistry* 14, 909-914
24. Decker, G., Wanner, G., Zenk, M. H., and Lottspeich, F. (2000) *Electrophoresis* 21, 3500-3516
25. Ghosal, S., Majumdar, S. K., and Chakraborti, A. (1971) *Austral. J. Chem.* 24, 2733-2735
26. Cacace, S., Schröder, G., Wehinger, E., Strack, D., Schmidt, J., and Schröder, J. (2003) *Phytochemistry* 62, 127-137
27. Small, L. F., and Lutz, R. E. (1932) *Chemistry of the Opium Alkaloids*, Supplement No. 103, Public Health Reports, Washington, p. 34
28. Sekine, Y., Creveling, C., Bell, M., and Brossi, A. (1990) *Helv. Chim. Acta* 73, 426-432
29. Fisinger, U. Dissertation zur Erlangung des Doktorgrades der Fakultät für Chemie und Pharmazie der Ludwig-Maximiliens-Universität zu München: "Untersuchungen zur Morphinbiosynthese in der Ratte *Rattus rattus* L. und im Schlafmohn *Papaver somniferum* L." 1998.
30. Decker, G. T. Dissertation zur Erlangung des Doktorgrades der Fakultät für. Chemie und Pharmazie der Ludwig-Maximiliens-Universität zu München: "Der Milchsaft von *Papaver somniferum*. Die Proteinanalyse als Ansatz zur Funktionsanalyse" 2001.
31. Facchini, P. J. and Park, S. U. GenBank accession n° AY217335.
32. Li et al., (1997), PNAS 94, 5461-5466.

The invention claimed is:

1. Isolated or purified protein having (R,S)-reticuline 7-O-methyltransferase activity, said protein comprising:
   i) the amino acid sequence illustrated in FIG. 9 (SEQ. ID NO: 2), or
   ii) a fragment of the amino acid sequence illustrated in FIG. 9 (SEQ. ID NO: 2), said fragment comprising an N- or C-terminal truncation of said amino acid sequence and having at least 350 amino acids, or
   iii) a variant of the amino acid sequence of FIG. 9 (SEQ. ID NO: 2), said variant having at least 95% identity with the amino acid sequence of FIG. 9 (SEQ. ID NO: 2) over a length of at least 350 amino acids and having amino acid motifs LVDVGGG LVDGGG, PXXDAXXMK, XGKVI, DLPHV, HVGGDMF, and GKERT, wherein X represents any amino acid and wherein said amino acid sequence of i), said fragment of ii), and said variant of iii) possesses (R,S)-reticuline 7-O-methyltransferase activity.

2. The protein according to claim 1 which is a dimer comprising two protein sub-units, each sub-unit being chosen from any one of proteins (i), (ii) or (iii) as defined in claim 1.

3. The protein according to claim 1, having at least 95.5% to 99.9% identity with the amino acid sequence of FIG. 9 (SEQ. ID NO: 2) over a length of at least 350 amino acids and having amino acid motifs LVDVGGG, PXXDAXXMK, XGKVI, DLPHV, HVGGDMF, and GKERT, wherein X represents any amino acid.

* * * * *

UNITED STATES PATENT AND TRADEMARK OFFICE
CERTIFICATE OF CORRECTION

PATENT NO. : 7,514,251 B2  Page 1 of 1
APPLICATION NO. : 10/888656
DATED : April 7, 2009
INVENTOR(S) : Toni M. Kutchan and Anan Ounaroon It is certified that error appears in the above-identified patent and that said Letters Patent is hereby corrected as shown below:

Title page, in Item (75) Inventors: "Bangkae" should be replaced by "Phitsanulok" and "Stefanie Haase, Werben (DE); Susanne Frick, Augsburg (DE)" should be removed.

Signed and Sealed this

Second Day of June, 2009

JOHN DOLL
*Acting Director of the United States Patent and Trademark Office*